(12) United States Patent
Hori et al.

(10) Patent No.: US 9,631,014 B2
(45) Date of Patent: Apr. 25, 2017

(54) METHOD AND REAGENT FOR DIAGNOSIS AND/OR EVALUATION OF PROGRESSION OF GRAFT-VERSUS-HOST DISEASE

(71) Applicant: Sapporo Medical University, Hokkaido (JP)

(72) Inventors: Tsukasa Hori, Hokkaido (JP); Yasuo Kokai, Hokkaido (JP); Yasuyoshi Naishiro, Hokkaido (JP); Hiroyuki Tsutsumi, Hokkaido (JP); Kohzoh Imai, Hokkaido (JP)

(73) Assignee: SAPPORO MEDICAL UNIVERSITY, Hokkaido (JP)

(*) Notice: Subject to any disclaimer, the term of this patent is extended or adjusted under 35 U.S.C. 154(b) by 515 days.

(21) Appl. No.: 14/244,166

(22) Filed: Apr. 3, 2014

(65) Prior Publication Data
US 2014/0234335 A1 Aug. 21, 2014

Related U.S. Application Data

(60) Division of application No. 13/523,791, filed on Jun. 14, 2012, now abandoned, which is a continuation of application No. 12/666,209, filed as application No. PCT/JP2008/001625 on Jun. 23, 2008, now abandoned.

(30) Foreign Application Priority Data

Jun. 22, 2007 (JP) ................. 2007-165547

(51) Int. Cl.
| | | |
|---|---|---|
| A61K 39/395 | (2006.01) | |
| C07K 16/24 | (2006.01) | |
| G01N 33/68 | (2006.01) | |
| A61K 39/00 | (2006.01) | |
| G01N 30/88 | (2006.01) | |

(52) U.S. Cl.
CPC ......... *C07K 16/24* (2013.01); *G01N 33/6863* (2013.01); *A61K 2039/505* (2013.01); *G01N 2030/8831* (2013.01); *G01N 2333/523* (2013.01); *G01N 2800/245* (2013.01)

(58) Field of Classification Search
None
See application file for complete search history.

(56) References Cited

U.S. PATENT DOCUMENTS

| | | | |
|---|---|---|---|
| 7,498,023 B2* | 3/2009 | Sykes | A61K 35/17 424/577 |
| 2004/0022841 A1 | 2/2004 | Hassan et al. | |
| 2005/0025768 A1 | 2/2005 | De Fougerolles et al. | |
| 2006/0105367 A1 | 5/2006 | Mischak | |
| 2006/0233710 A1 | 10/2006 | Matsushima et al. | |
| 2007/0014785 A1 | 1/2007 | Golay et al. | |
| 2007/0134236 A1 | 6/2007 | De Fougerolles et al. | |

FOREIGN PATENT DOCUMENTS

| | | |
|---|---|---|
| JP | 2003-521927 | 7/2003 |
| JP | 2007-051980 A | 3/2007 |
| WO | WO 01/57226 A1 | 8/2001 |
| WO | 03/048083 A2 | 6/2003 |
| WO | 2005032589 A1 | 4/2005 |
| WO | WO 2007/024715 A9 | 3/2007 |

OTHER PUBLICATIONS

Wysocki et al. Blood. 2005;105: 4191-4199.*
Berger et al. (Bone Marrow Transplantation, (Apr. 2012) vol. 47, Suppl. 1, pp. S323-S324. Abstract No. P891).*
Berger et al. (Bone Marrow Transplantation (2013) 48, 1230-1236).*
Abdi et al., "Differential Role of CCR2 in Islet and Heart Allograft Rejection: Tissue Specificity of Chemokine/Chemokine Receptor Function in Vivo," *Journal of Immunology*, vol. 172, No. 8, pp. 767-775 (2004).
Advisory Action mailed May 1, 2012, in U.S. Appl. No. 12/666,209.
Amendment After Final under 37 C.F.R. § 1.116 filed Apr. 16, 2012, in U.S. Appl. No. 12/666,209.
Cao et al., "Chemokines and Chemokine Receptors Induced Lymphocyte Migration and Graft-versus-host Disease," *Chinese Journal of Cell Biology*, vol. 28, pp. 808-812 (2006).
Choi et al., "The Profiles of Plasma Chemokines Following Unrelated Allogeneic Bone Marrow Transplantation and Their Relationship to Transplant-Related Complications," *Journal of Bacertiology and Virology*, vol. 33, No. 4, pp. 317-327 (2003).
Database WPI Week 200724, Thompson Scientific, London, GB; AN 2007-235648 & JP 2007/051980 A, Univ. Okayama, Mar. 1, 2007.
European Office Action dated Jun. 12, 2012, in European Application No. 08764208.8.
Final Office Action mailed Dec. 14, 2011, in U.S. Appl. No. 12/666,209.
Hess et al., "Decidual Stromal Cell Response to Paracrine Signals from the Trophoblast: Amplification of Immune and Angiogenic Modulators," *Biology of Reproduction*, 79: 102-117 (2007) (available online Oct. 4, 2006).
Hori et al., "CCL8 is a Potential Molecular Candidate for the Diagnosis of Graft-Versus-Host Disease," *Blood*, vol. 111, No. 8, pp. 4403-4412 (Apr. 15, 2008).
Ichiba et al., "Early changes in gene expression profiles of hepatic GVHD uncovered by oligonucleotide microarrays," *Blood*, 102(2): 763-771 (2003).

(Continued)

*Primary Examiner* — Zachary Skelding
(74) *Attorney, Agent, or Firm* — Pearne & Gordon LLP

(57) ABSTRACT

Disclosed is a method of diagnosing graft-versus-host disease, comprising measuring the level of CCL8 protein in a sample obtained from a subject as an indicator for the diagnosis or course of graft-versus-host disease. Also a diagnostic reagent for graft-versus-host disease comprising an anti-CCL8 antibody is disclosed. The method of the present invention enables diagnosis of the onset of graft-versus-host disease and monitoring of the progress, in particular, differential diagnosis between graft-versus-host disease and an infectious disease. The present invention also provides a method for treating graft-versus-host disease utilizing the anti-CCL8 antibody.

7 Claims, 17 Drawing Sheets

(56) References Cited

OTHER PUBLICATIONS

International Search Report from the Japanese Patent Office for International Application No. PCT/JP2008/001625, mailed Jul. 29, 2008.

Kaiser et al., "Proteomics Applied to the Clinical Follow-Up of Patients After Allogeneic Hematopoietic Stem Cell Transplantation," *Blood*, vol. 104, No. 2, pp. 340-349, (Jul. 15, 2004).

Miura et al., "Non-Invasive Diagnosis of Acute Rejection by Measuring Chemokinegene Expression in Urine of Kidney Transplant recipients," (Abstract Only) *Journal of Urology*, vol. 171, No. 4 Supplement, pp. 490, (2004).

Murai et al., "Involvement of Chemokine in Liver-Infiltrating CD8 Cells Induced by Acute GVHD," *Proceedings of the Japanese Society for Immunology*, vol. 28, p. 152, 3-A4-111 (1998).

Murai et al., "Kyusei GVHD ni yoru Kan Shinjun CD8 Saibo ni Okeru Chemokine no Kan'yo," *Proceedings of the Japanese Society for Immunology*, (Abstract Only) vol. 28, 3-A4-111, p. 152 (1998).

Nomura et al., "Role of Platelet-Derived Chemokines (RANTES and ENA-78) after Stem Cell Transplantation," *Transplant Immunology*, vol. 15, No. 4, pp. 247-253, (2006).

Office Action dated Jul. 9, 2013, issued in Japanese Patent Application No. 2009-520345.

Office Action mailed Mar. 28, 2011, in U.S. Appl. No. 12/666,209.

Office Action mailed Oct. 4, 2013, in U.S. Appl. No. 13/523,791.

Panoskaltsis-Mortari et al., "Amelioration of Idiopathic Pneumonia Syndrome (IPS) and GVHD by KGF-Pretreatment is Partly Mediated Via a STAT-6-Dependent Pathway in the Host," (Abstract Only) *Blood*, vol. 108, No. 11, Part 1, p. 910A, (2006).

Petricoin III et al., "Use of Proteomic Patterns in Serum to Identify Ovarian Cancer," *The Lancet*, vol. 359, pp. 572-577 (Feb. 16, 2002).

Response to Restriction Requirement filed Feb. 28, 2011, in U.S. Appl. No. 12/666,209.

Response to Restriction Requirement filed Apr. 11, 2013, in U.S. Appl. No. 13/523,791.

Response to Office Action filed Sep. 27, 2011, in U.S. Appl. No. 12/666,209.

Restriction Requirement mailed Dec. 27, 2010, in U.S. Appl. No. 12/666,209.

Restriction Requirement mailed Mar. 13, 2013, in U.S. Appl. No. 13/523,791.

Schadde et al., "Review: chemokines in transplantation," *Transplantation Reviews*, 21: 107-118 (Apr. 2007).

Schultz et al., "Toward Biomarkers for Chronic Graft-verus-Host Disease: National Institutes of Health Consensus Development Project on Criteria for Clinical Trials in Chronic Graft-versus-Host Disease: III. Biomarker Working Group Report," *Biology of Blood and Marrow Transplantation*, 12:126-137 (2006).

Shots et al., "Proinflammatory cytokines and their role in the development of major transplant-related complications in the early phase after allogeneic bone marrow transplantation," *Leukemia* 17: 1150-1156 (2003).

Sugerman et al., "Kinetics of Gene Expression in Murine Cutaneous Graft-versus-Host Disease," *American Journal of Pathology*, 164(6): 2189-2202 (2004).

Sullivan, "Graft-vs.-Host Disease," *Thomas' Hematopoietic Cell Transplantation*, Third Edition, Malden, MA, Blackwell Publishing, pp. 635-664, (2004).

Supplementary European Search Report from the European Patent Office for Application No. 08764208.8 (International Patent Application No. PCT/JP2008/001625), mailed May 7, 2010.

Ziegler et al., "Chemokine Profiling in Patients with Graft Versus Host Disease (GVHD) Following Allogeneic Blood Stem Cell Transplantation," (Abstract Only) *Blood*, vol. 108, No. 11, Part 1, pp. 814A-815A, (2006).

Office action in related Russian application 2012157473, dated Feb. 10, 2017.

\* cited by examiner

NO ONSET OF GVHD

| POST-TRANSPLANTATION DAY 14 | LIVER | | | | INTESTINE | | | | SKIN | | | |
|---|---|---|---|---|---|---|---|---|---|---|---|---|
| | + | +/− | − | | + | +/− | − | | + | +/− | − | |
| CONTROL IgG | 3 | 0 | 0 | | 3 | 0 | 0 | | 3 | 0 | 0 | |
| ANTI-MOUSE CCL8 IgG | 3 | 0 | 0 | | 2 | 1 | 0 | | 0 | 2 | 1 | |

Fig.17

METHOD AND REAGENT FOR DIAGNOSIS AND/OR EVALUATION OF PROGRESSION OF GRAFT-VERSUS-HOST DISEASE

CROSS REFERENCE TO RELATED APPLICATIONS

This is a divisional application of U.S. application Ser. No. 13/523,791, filed Jun. 14, 2012, which is continuation application of U.S. application Ser. No. 12/666,209, whose 35 U.S.C. §371(c) date is Mar. 15, 2010, which is a national stage of International Application No. PCT/JP2008/001625, filed Jun. 23, 2008, all of which claim priority to Japanese Patent Application No. 2007-165547, filed Jun. 22, 2007, and the entire disclosures of all of which are incorporated herein by reference.

TECHNICAL FIELD

The present invention relates to a method and reagent for diagnosis of graft-versus-host disease, as well as a method and a pharmaceutical composition for treating graft-versus-host disease.

BACKGROUND ART

Hematopoietic stem cell transplantation (HSCT) is a therapy where hematopoietic stem cells from another individual is transplanted into a patient to restore hematopoiesis and immune function, and it has been established as a mode of therapy in a broad range of blood, tumor, metabolism, and immune diseases. Post-transplantation immunosuppression therapy has made considerable progress in the last 20 years, but graft-versus-host disease (GVHD) continues to be a major, life-threatening post-transplantation complication. Despite preventive therapy using immunosuppressants, GVHD occurs in 30 to 80% of HSCT recipients (patients). Therefore, early diagnosis of GVHD, early initiation of therapy, and objective monitoring of therapeutic efficacy are needed. Moreover, current therapeutic methods do not always result in a cure, and the development of new therapeutic methods is needed. For information about the incidence, diagnosis, and treatment of GVHD, see the report by Sullivan et al. (Sullivan K M. Graft vs. host disease. In: Blume K G, Forman S J, Appelbaum F R, eds. Thomas' Hematopoietic Cell Transplantation. 3rd ed. Malden, Mass.: Blackwell Publishing; 2004:635-664).

At present, however, the diagnosis of GVHD is mainly carried out based on clinical findings such as skin rash, hyperbilirubinemia, diarrhea, etc., and no determinative biomarker exists that can distinguish GVHD from other similar complications (veinous occlusion, viral reactivation, a treatment regimen-related toxicity, and the like). Therefore, an invasive method such as liver biopsy is required for a differential diagnosis of GVHD. However, as biopsy is an invasive and subjective diagnostic method, it is desired to develop a new method that can facilitate early, accurate, and objective quantitative diagnosis of GVHD without reliance on biopsy, leading to suitable therapy for GVHD and improvement of the outcome of HSCT.

Recent advances in proteomics have provided several methods for investigating global protein expression in biological fluids and identifying a new biomarker for the disease or pathological conditions. One such method is surface-enhanced laser desorption/ionization time-of-flight mass spectrometry (SELDI-TOF MS). This is a high-throughput, highly sensitive proteomic approach for isolating proteins from a body fluid with a complex composition such as plasma to generate a comparative protein profile. Petricoin et al. (Petricoin E F, Ardekani A M, Hitt B A, et al. Use of proteomic patterns in serum to identify ovarian cancer. Lancet. 2002; 359:572-577) have reported a biomarker for ovarian cancer based on proteomic analysis using SELDI. In SELDI, proteins obtained from a biological sample are allowed to selectively bind to chemically modified affinity surfaces on a ProteinChip (Ciphergen Biosystems, Fremont, Calif.), and then nonspecifically bound impurities are washed away. Next, the captured proteins are analyzed by TOF-MS to obtain a spectrum of the molecular mass of each protein (m/z) and relative concentration (intensity). Through recent studies this type of technologies have been successfully applied to the diagnosis of cancer and other diseases.

Recent reports describe proteomic analysis of body fluids from GVHD patients. In tests using human clinical samples, however, artifacts related to genetic background and the environment are unavoidable, and this has confounded the discovery of a new biomarker. This is particularly true for post-HSCT patients, who have a wide variety of pre-existing diseases, and undergo diverse conditioning regimens and GVHD prophylaxis. There have been no reports of the discovery of a useful marker based on biochemical methods including proteomic analysis. For example, Kaiser et al. (Kaiser T, Kamal H, Rank A, et al. Proteomics applied to the clinical follow-up of patients after allogeneic hematopoietic stem cell transplantation. Blood. 2004; 104:340-349) report on their investigation of GVHD markers by proteomic analysis using urine as a sample. Two proteins (a leukotriene, i.e., an inflammation mediator, and serum albumin, i.e., the most frequent protein in serum) were identified, but no GVHD-specific protein was found.

The reference documents cited in the present description are listed below. The contents of these publications are hereby incorporated by reference in its entirety. However, none of these documents is admitted to be prior art of the present invention.

Non-patent document 1: Sullivan K M. Graft vs. host disease. In: Blume K G, Forman S J, Appelbaum F R, eds. Thomas' Hematopoietic Cell Transplantation. 3rd ed. Malden, Mass.: Blackwell Publishing; 2004:635-664

Non-patent document 2: Petricoin E F, Ardekani A M, Hitt B A, et al. Use of proteomic patterns in serum to identify ovarian cancer. Lancet. 2002; 359:572-577

Non-patent document 3: Kaiser T, Kamal H, Rank A, et al. Proteomics applied to the clinical follow-up of patients after allogeneic hematopoietic stem cell transplantation. Blood. 2004; 104:340-349

DISCLOSURE OF THE INVENTION

An object of the present invention is to provide a method and reagent for diagnosis of GVHD, and a method and a pharmaceutical composition for treating GVHD.

The present inventors investigated a broad range of proteins that are expressed differently in a GVHD model animal and a control animal, and discovered that the expression level of CCL8 is significantly higher in GVHD. Additionally, they discovered that there is a correlation between the expression level of CCL8 and the manifestation of clinical signs and course of GVHD, to achieve the present invention.

The present invention provides a method for testing GVHD comprising measuring the level of CCL8 protein in a sample obtained from a human subject or animal subject as an indicator for diagnosis or course of GVHD. Preferably, the diagnosis of GVHD is made before the manifestation of clinical signs.

In the method of the present invention, preferably the level of CCL8 protein is measured using an anti-CCL8 antibody. Also preferably the level of CCL8 protein is measured using a method selected from the group consisting of mass spectrometry (MS), high-performance liquid chromatography (HPLC), and two-dimensional electrophoresis.

The present invention also provides a diagnostic reagent for GVHD comprising an anti-CCL8 antibody.

The present invention also provides a method for selecting a candidate substance for a therapeutic agent for GVHD. This method comprises the steps of: administering the test substance to a GVHD model animal; measuring the level of CCL8 protein in a sample obtained from the model animal; and selecting the test substance as a candidate substance for a therapeutic agent for GVHD if the CCL8 protein expression level is lower than the level without administration of the test substance.

The present invention also provides a pharmaceutical composition for treating GVHD comprising an anti-CCL8 antibody as an active ingredient. The present invention also provides a method for treating GVHD comprising administering an anti-CCL8 antibody to a subject suffering from graft-versus-host disease.

In accordance with the present invention, the development and course of GVHD is diagnosed in a highly reliable manner, leading to objective (rather than subjective as in the conventional method), quantitative, and more accurate diagnosis of GVHD. Furthermore, the present invention allows treatment of GVHD especially in patients resistant to existing therapeutic methods.

BRIEF DESCRIPTION OF THE DRAWINGS

FIG. 17 shows the pathological evaluation of therapeutic efficacy of the anti-CCL8 antibody in a GVHD model mouse.

PREFERRED EMBODIMENTS OF THE INVENTION

Figure 1:
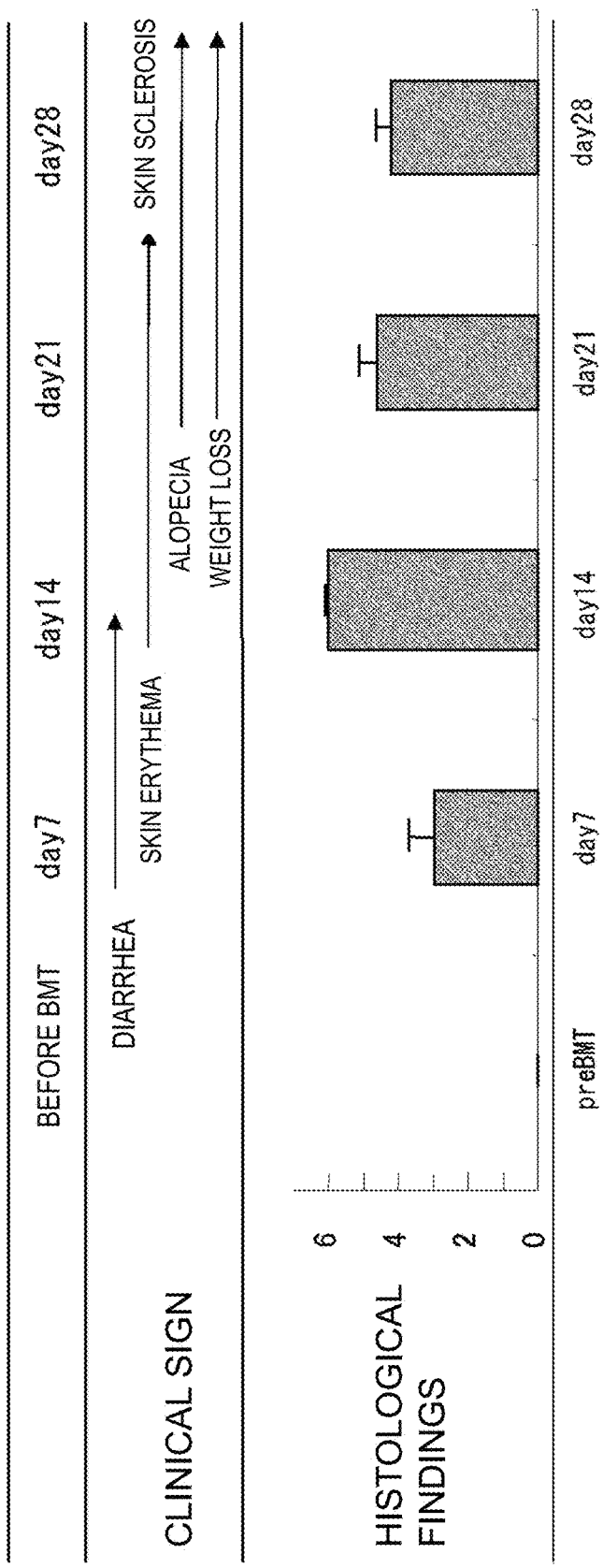
FIG. 1 shows the time course of clinical signs and pathology scores in a GVHD model mouse.

The present invention features a method for diagnosing GVHD and monitoring the course of GVHD by measuring the expression level of CCL8 in a test sample such as blood from a subject. As specifically illustrated in the following examples, among patients that have undergone bone marrow transplantation or umbilical cord blood transplantation, those who develop GVHD shows significantly higher expression level of CCL8, and a correlation was found between the manifestation of clinical signs of GVHD and the expression level of CCL8.

CCL8 is a basic, heparin-binding secretory protein belonging to the chemokine family, also called MCP-2 (GenBank Accession No. NP_005614). This protein is produced in monocytes, fibroblasts, epithelial cells, etc., and is known to bind to receptors CCR2, CCR3, CCR5 and CCR11. It has been shown that CCL8 targets CD4-positive T cells, CD8-positive T cells, monocytes, NK cells, eosinophils, basophils, and the like. It is believed that GVHD develops through 3 steps subsequent to hematopoietic stem cell transplantation (HSCT). The first step is conditioning, which includes exposure to radiation for preparing the host (patient) for HSCT; the second step is the activation, proliferation, and differentiation of transplanted T cells; and the third step is the appearance of cell-mediated or inflammatory effectors (for the mechanisms, see the following two reviews: Reddy P. Pathophysiology of acute graft-versus-host disease. Hematol Oncol. 2003; 21:149-161, Ferrara J L, Reddy P. Pathophysiology of graft-versus-host disease. Semin Hematol. 2006; 43:3-10). In the second step, antigen presentation by dendrocytes is necessary for activation of transplanted T cell. Chemokines including CCL8 play an important role in the differentiation, proliferation, and activation of these dendrocytes (for the importance of chemokines in the second step, see: Wysocki C A, Panoskaltsis-Mortari A, Blazar B R, Serody J S. Leukocyte migration and graft-versus-host disease. Blood. 2005; 105:4191-4199). However, the role of CCL8 in the body and its significance in regulation of the immune system are not fully understood. Therefore, the mechanism underlying the correlation between the expression of CCL8 and GVHD that was discovered in the present invention is still unknown.

A test sample to be measured for the level of CCL8 protein includes, for example, body fluid, blood, serum, and plasma from a human subject or animal subject. Tissue and cells collected from a subject may also be used as a test sample.

The amount of CCL8 protein in a test sample obtained from a subject can be measured by using an anti-CCL8 antibody in immunological assay methods well known in the art. The anti-CCL8 antibody may be a polyclonal antibody or a monoclonal antibody. Various types of anti-CCL8 polyclonal antibodies and monoclonal antibodies are commercially available, and any of these antibodies can be used in the present invention.

Alternatively, an antibody can be prepared by any of the methods well known in the art. A polyclonal antibody that binds to CCL8 can be obtained by a well-known method in the art that involves immunizing an animal using CCL8 or a peptide fragment thereof as the sensitizing antigen, isolating antiserum containing the antibody from the immunized animal, and verifying the presence of an antibody with the desired binding specificity by an ELISA assay, Western blot analysis, radioimmunoassay and the like.

A monoclonal antibody that binds to CCL8 can be obtained in accordance with a well-known method in the art that involves immunizing an animal using CCL8 or a peptide fragment thereof as the sensitizing antigen, collecting the resulting immune cells and fusing them with myeloma cells, selecting a hybridoma producing the antibody, and culturing the hybridoma.

The anti-CCL8 monoclonal antibody used in the present invention encompasses not only antibodies produced by hybridomas, but also recombinant antibodies produced by transformants transfected with an expression vector carrying the antibody gene. A recombinant antibody can be produced by cloning cDNA encoding a monoclonal antibody that binds to CCL8 from an antibody-producing hybridoma, inserting the cDNA into an expression vector, transforming an animal cell or a plant cell with the vector, and culturing the transformant. Alternatively, the gene encoding the anti-CCL8 antibody may be introduced into a transgenic animal to obtain the anti-CCL8 antibody produced in the transgenic animal.

For use in treating a human patient, it is preferable for the anti-CCL8 antibody of the present invention to be a human chimeric antibody or humanized antibody. A human chimeric antibody is an antibody constructed from an antibody heavy-chain variable region and light-chain variable region of an nonhuman animal, and a heavy-chain constant region and light-chain constant region of a human antibody. A humanized antibody is constructed from an antibody complementarity determining region (CDR) originating in a nonhuman animal and a framework region (FR) and C region originating in a human antibody. Human chimeric antibodies and humanized antibodies will have reduced antigenicity in the human body, and therefore are useful as an active ingredient of the pharmaceutical composition of the present invention. Conventional gene recombination techniques for obtaining human chimeric antibodies and humanized antibodies, and the methods for evaluating the binding activity of these antibodies are well known in the art. Alternatively, an anti-CCL8 human antibody can be obtained by introducing CCL8 into a transgenic animal having a complete repertoire of human antibody genes.

In addition, an antibody fragment may also be used in the present invention. An antibody fragment refers to a peptide that lacks a part of the entire anti-CCL8 antibody but still has CCL8 binding capability. Examples of antibody fragments include Fab, Fab', F(ab')2, Fv, and the like. The antibody fragment can be obtained by enzymatic treatment of the antibody to produce fragments. The antibody fragment of the present invention also includes antibody fragments and dimers thereof constructed by joining a VL chain and VH chain of an anti-CCL8 antibody with a linker. Examples include an ScFv, diabody, sc(Fv)$_2$, and the like.

The CCL8 protein in a test sample obtained from a human subject or animal subject is assayed by an immunological method using an antibody obtained in this manner. The assay may be qualitative or quantitative. An immunoassay for the expression of CCL8 in a sample obtained from a subject can be carried out using a radioimmunoassay, ELISA, immunoprecipitation, immunoagglutination, Western blotting, and the like.

As a typical example, sandwich ELISA can be carried out in the following manner. Peripheral blood is collected from the subject and plasma is prepared, added to a plate or chip where the anti-CCL8 antibody is immobilized, and incubated for a suitable period of time. After the plate or chip is washed to remove unbound components, another anti-CCL8 antibody is added. The antibody can be detectably labeled with an enzyme, fluorescent dye, chemoluminescent substance, biotin, radioactive compound, and the like. After incubation for a suitable period of time, the plate or chip is washed, and the label is detected by fluorescence, luminescence, radioactivity, and the like. Optionally, after the anti-CCL8 antibody is bound to the protein, a secondary antibody (for example, goat anti-mouse antibody) may be added in order to amplify the signal. The secondary antibody can be detectably labeled with an enzyme, fluorescent dye, chemoluminescent substance, biotin, radioactive compound, and the like. The amount of CCL8 protein in plasma obtained from the subject can be measured in this manner.

In another aspect, the CCL8 protein can be detected using a detection method involving an agglutination reaction. In this method CCL8 can be detected using a carrier, for example latex particles carrying the anti-CCL8 antibody. When the latex particles carrying the anti-CCL8 antibody are mixed with the test sample and incubated for a predetermined period of time, the particles will agglutinate if CCL8 is contained in the sample. The CCL8 in the sample can be detected by observing the extent of the agglutination with the naked eye or by quantifying using a spectrophotometer.

In still another aspect, the CCL8 protein can be detected using a biosensor utilizing the surface plasmon resonance phenomenon. A biosensor based on the surface plasmon resonance phenomenon enables monitoring protein-protein interactions as a surface plasmon resonance signal. For example, binding between the CCL8 protein and the anti-CCL8 antibody can be detected using a biosensor such as BIAcore (Pharmacia). More specifically, the test sample is brought into contact with a sensor chip having the anti-CCL8 antibody and the CCL8 protein bound to the anti-CCL8 antibody can be detected as a change in the resonance signal.

In another embodiment, the test sample is partially purified (enriched) using a metal chelating agent and an affinity support such as heparin, and the CCL8 protein can be detected and quantified by MS, as shown in Example 2. Furthermore, the CCL8 protein can be detected and quantified by HPLC as shown in Example 3, or it can be detected and quantified by two-dimensional electrophoresis and silver staining.

The present invention also provides a diagnostic reagent for GVHD comprising an anti-CCL8 antibody. The diagnostic reagent for GVHD of the present invention can be provided in the form of a test kit. The test kit contains a reagent for detecting CCL8, e.g., an anti-CCL8 antibody, as the active ingredient. The kit may also contain suitable reagents necessary for the assay such as a buffer solution, diluent, reaction stopping solution, washing solution, control sample, and the like.

Figure 14:
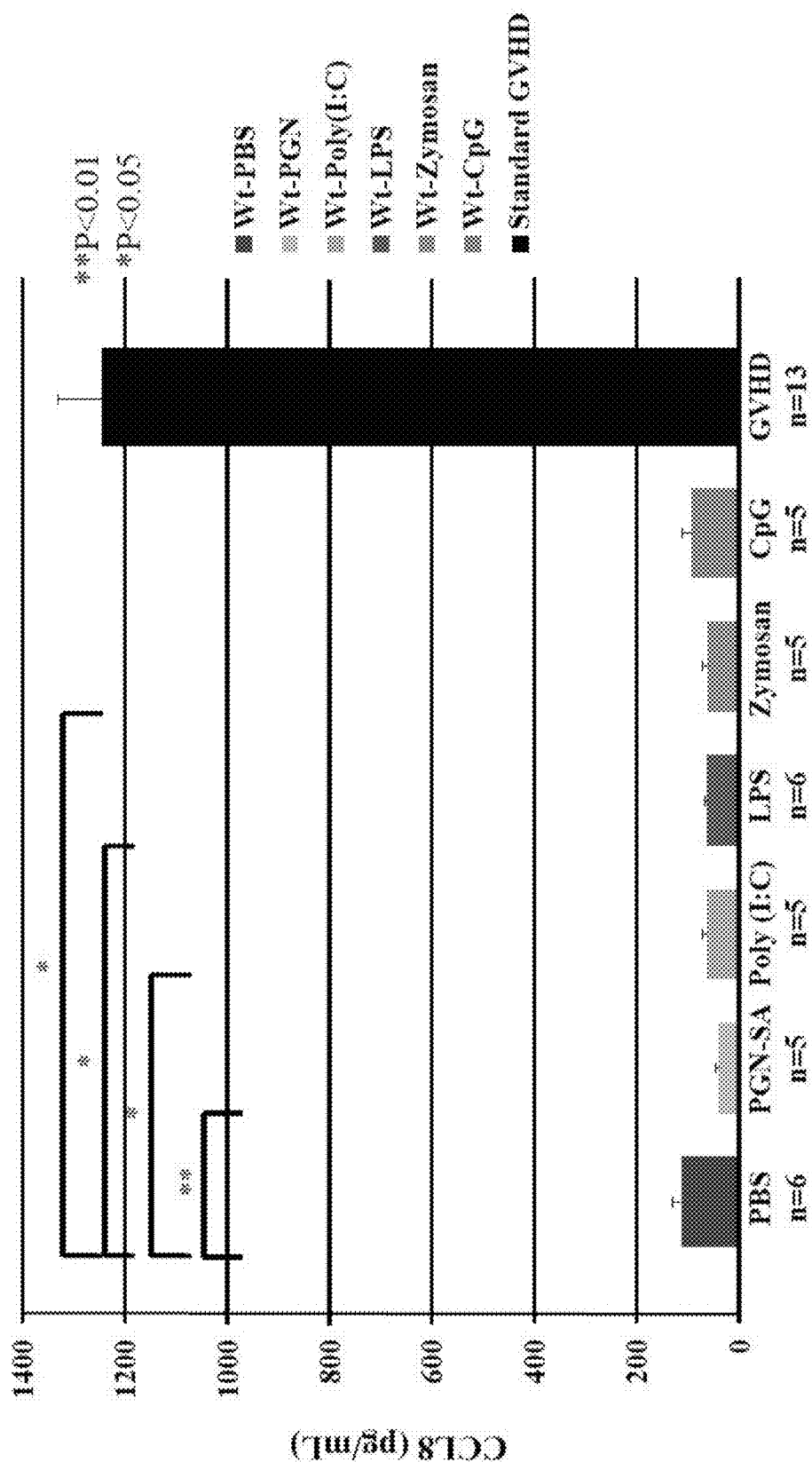
FIG. 14 shows the time course of the CCL8 protein level in a mouse receiving TLR ligand and in a GVHD model mouse.

In the present invention, the level of CCL8 protein measured in this manner may be used as an indicator for diagnosis of GVHD. According to the present invention, GVHD can be diagnosed objectively by using the CCL8 protein as a marker rather than depending on observations such as visual examination and the amount of diarrhea, and thus the development and course of GVHD can be monitored. The diagnostic method of the present invention is useful, for example, for diagnosis before the manifestation of GVHD (early diagnosis), definitive diagnosis of the development, scoring of severity, monitoring the course of the disease, evaluating therapeutic efficacy and prognosis. In particular, as shown in FIG. 14, the expression level of CCL8 does not increase via a pathway mediated by TLR (Toll-like receptor), which allows differential diagnosis between GVHD and a bacterial or viral infection using the CCL8 protein as a marker.

Figure 8:
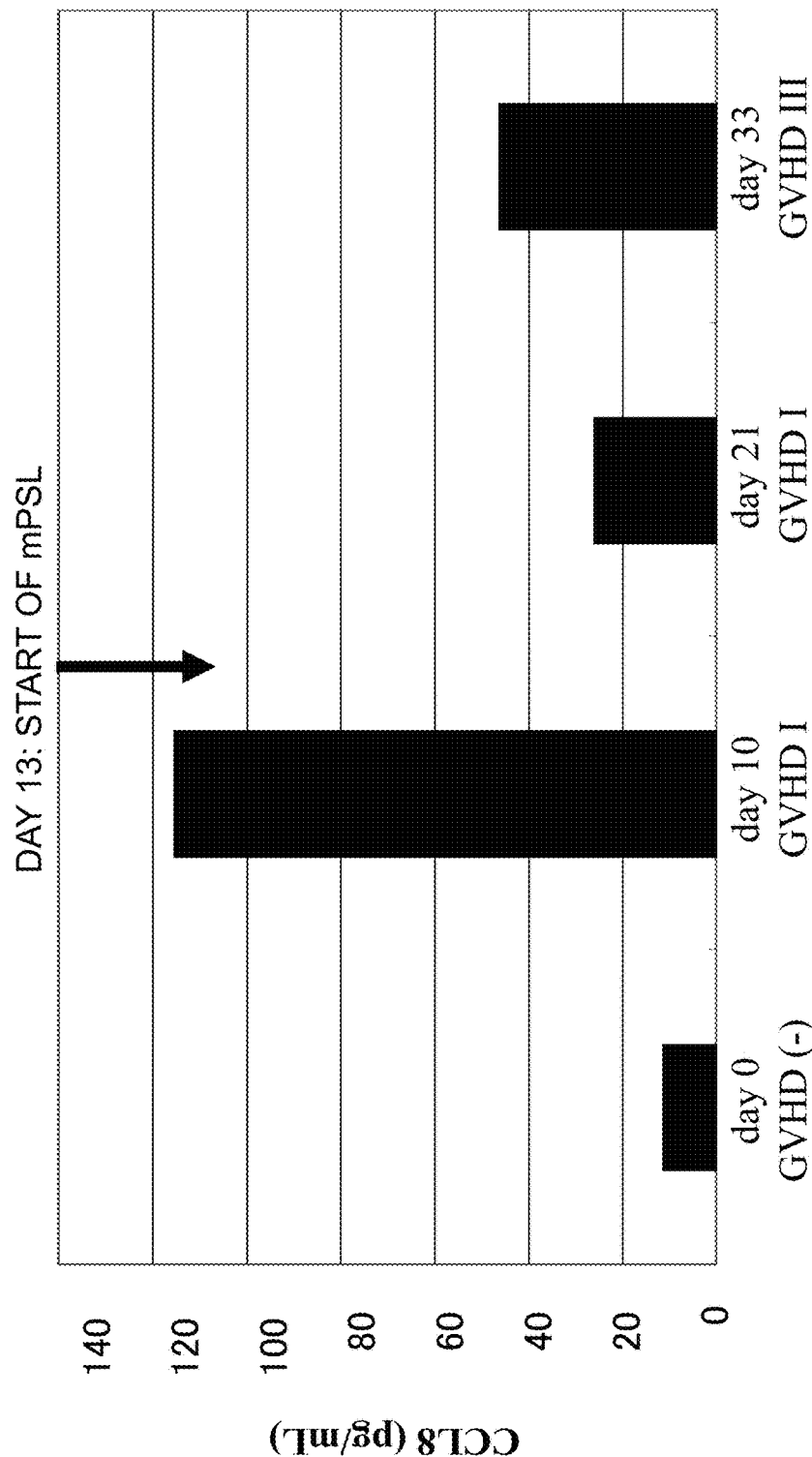
FIG. 8 shows the time course of the CCL8 protein level in a human clinical sample.
Figure 9:
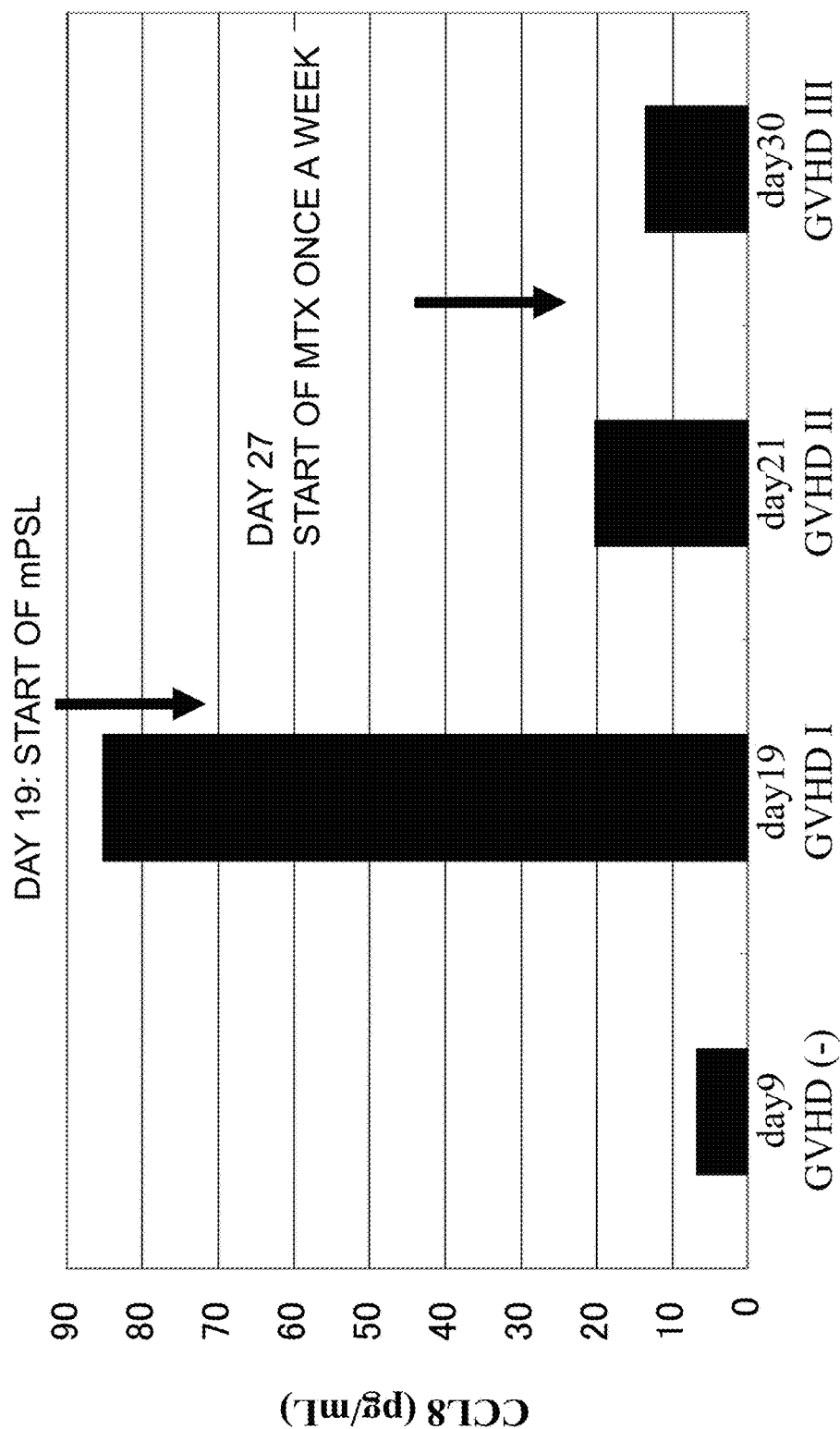
FIG. 9 shows the time course of the CCL8 protein level in a human clinical sample.

As shown in the following examples, the CCL8 expression level in patients is significantly higher after the development of GVHD than before the development. Example 8 demonstrates that in a bone marrow transplant model mouse, the amount of CCL8 expression began to increase two days before clinical signs of GVHD were recognized. In addition, as shown in FIGS. 8 and 9, the amount of CCL8 expression starts to increase before clinical signs of GVHD is observed in human patients as well, indicating that the method of the present invention enables early diagnosis of GVHD. Furthermore, the method of the present invention is useful for evaluating therapeutic efficacy. As shown in FIGS. 8 and 9, as the clinical signs of GVHD improved through therapy, a decrease in the CCL8 expression level was observed. In treatment-resistant GVHD, conventional methylprednisolone therapy is not effective, and more aggressive treatment is required. Because such treatment is often accompanied by adverse side effects, it is beneficial to adjust the dose and control the therapy while suitably monitoring therapeutic efficacy by the method of the present invention.

Figure 11:
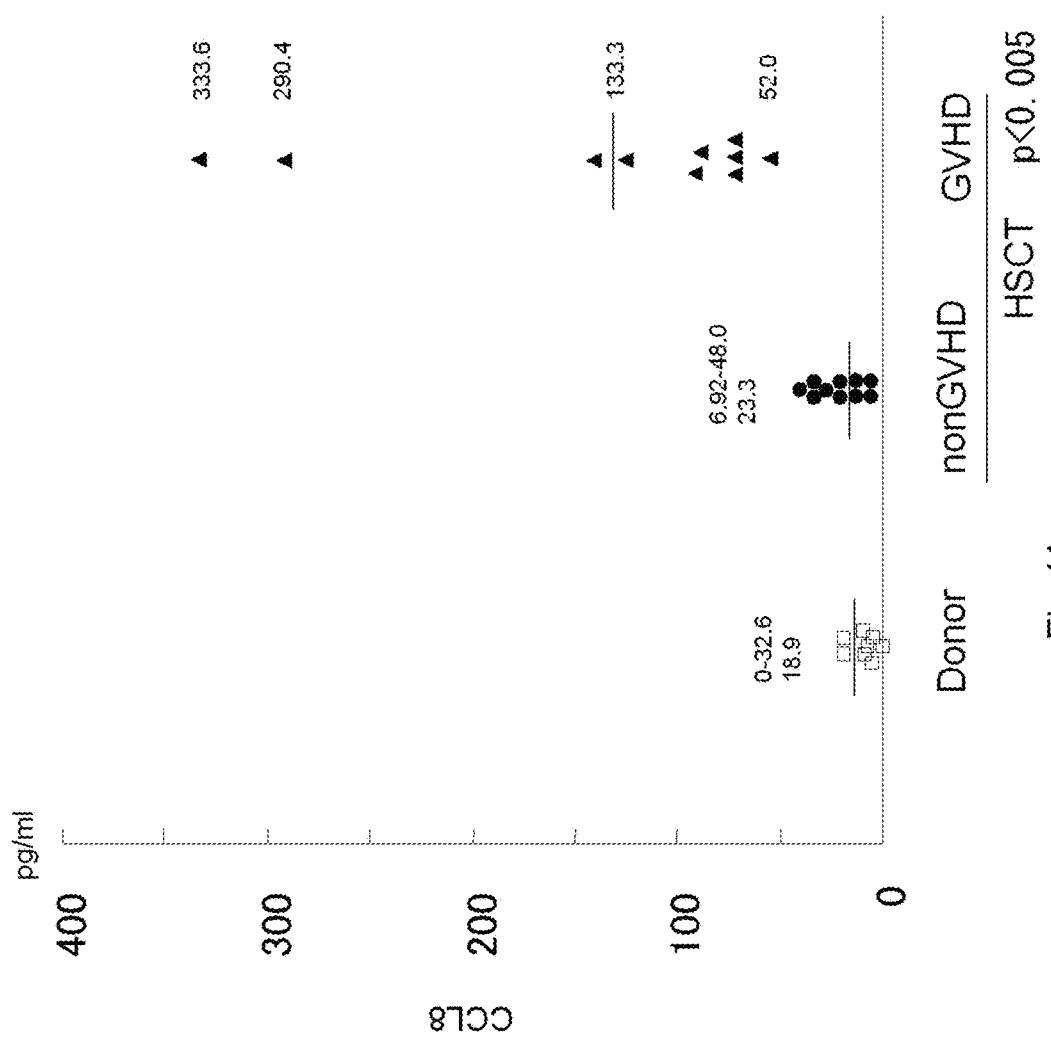
FIG. 11 shows the detection of the CCL8 protein in a plurality of human clinical samples.

Furthermore, as shown in FIG. 11, the CCL8 expression level correlates with the severity and prognosis of GVHD, thus the method of the present invention will enable earlier identification of patient with severe conditions and implementation of suitable proper treatments.

In addition, the method of the present application is useful for the development and improvement of therapeutic modes for GVHD. As shown in FIG. 11, patients with treatment-resistant GVHD can be identified by measuring the level of CCL8 expression. There is no established mode of therapy for such patients. A suitable therapeutic mode may be developed by studying the efficacy of combination therapy with multiple agents with monitoring the CCL8 level in the patients.

Furthermore, because at present no magic drug for GVHD is available, the present invention is also useful in screening for candidate substances that would be a powerful drug for the treatment of GVHD based on the CCL8 expression level as an indicator. Screening is carried out by administering a test substance to a GVHD model animal, and measuring the amount of CCL8 protein in a test sample obtained from the model animal. For example, an anti-CCL8 antibody can be used as a test substance. Also the test substance can be obtained from a library such as a library of various synthetic or naturally occurring compounds, a combinatorial library, oligonucleotide library, peptide library, and the like. The test substance may also include an extract of a natural substance or partially refined product originating in bacteria, fungi, algae, plants, animals and the like. If the level of CCL8 protein is lower in animals receiving the test substance, the test substance can be selected as a candidate substance for a therapeutic agent for GVHD. In other words, the diagnostic method of the present invention provides a platform for the development of new modes of therapy for GVHD.

In another aspect, the present invention provides a pharmaceutical composition for treating GVHD comprising an anti-CCL8 antibody as the active ingredient, as well as a method for the treatment of GVHD comprising administrating an anti-CCL8 antibody. As shown in Example 9 below, when an anti-CCL8 antibody was administered to a GVHD model animal and evaluating pathological conditions, a decrease in inflammatory cell infiltration into the dermoepidermal junction in the skin and amelioration of damage to hair follicles and sebaceous glands were observed, demonstrating that administration of the anti-CCL8 antibody is effective in the treatment of GVHD.

The pharmaceutical composition of the present invention may be formulated by a method known in the art. For example, the composition may be formulated by suitably combining with a pharmaceutically acceptable carrier or excipient, such as sterile water and physiological saline, vegetable oil, emulsifier, suspending agent, surfactant, stabilizer, flavoring, filler, vehicle, preservative, binder, and the like, and compounding them into the form of a unit dose required for generally recognized pharmaceutical manufacturing.

For oral administration, the compound of the present invention can be formulated into a tablet, pill, dragee, capsule, liquid, gel, syrup, slurry, suspension, and the like by admixing with a pharmaceutically acceptable carrier well known in the art.

For parenteral administration, the compound of the present invention can be formulated into an injectable, an aerosol spray, product for dermal administration and the like using a pharmaceutically acceptable vehicle well known in the art.

The pharmaceutical composition of the present invention can be administered to a patient by oral or parenteral administration. Parenteral administration is preferred. Examples of the route of administration include intravenous injection, intramuscular injection, intraperitoneal injection, subcutaneous injection, intrarectal administration, transnasal administration, transpulmonary administration, transcutaneous administration and the like. The dosage can be selected from a range of 0.0001 mg to 1000 mg/kg of body weight for a single dose. The route of administration and dose can be selected as needed by the attending physician in consideration of the age of the patient, severity of symptoms, concomitant drugs, and the like.

The content of all patents and reference documents specifically cited in the present description are hereby incorporated by reference in its entirety.

The present invention is described in greater detail below through the following examples, but is by no means limited by the examples.

Example 1

Bone Marrow Transplantation (BMT)

Acute GVHD was induced in mice via allogeneic bone marrow transplantation. BALB/c (H-$2^d$) mice were used as the recipients, C57BL/6 (H-$2^b$) mice were used as the allogeneic BMT donors, and BALB/c (H-$2^d$) mice were used as the syngeneic BMT donors. All mice were 7 to 12 weeks old (Sankyo Labo Service Corporation, Japan).

On the day of BMT, the donor mice were sacrificed by cervical dislocation. Donor bone marrow cells were collected by flushing the shaft of the femur and tibia. The cells were placed in modified Eagle's medium containing 2% fetal calf serum/1% penicillin-streptomycin, and prepared as a single cell suspension. The cells were rinsed with RPMI 1640 medium and resuspended in that same medium. The bone marrow cell inoculum was prepared to contain $2\times10^7$ bone marrow cells/200 µL for allogeneic BMT and $1\times10^6$ bone marrow cells/100 µL for syngeneic BMT.

The recipient BALB/c mice were raised on acidic water for at least 7 days before BMT to prevent sepsis after a lethal dose of radiation. The recipient mice were given a total of 8.5 Gy of total body irradiation at a rate of 0.34 Gy/min, and within 3 hours after irradiation the donor bone marrow cells were injected intravenously via the caudal vein.

Monitoring of GVHD

The recipient mice were observed every day for clinical signs of GVHD, i.e., weight loss, hunched posture, skin erythema, alopecia, and diarrhea. In the allogeneic BMT mice, clinical signs of acute GVHD, e.g., diarrhea and ruffled fur within 7 days post-transplantation, and skin erythema and alopecia within 21 days. Some animal deaths were found at days 14 and 21 post-transplantation.

Histopathologic Analysis

The recipient mice were sacrificed on post-transplantation days 7, 14, 21, and 28. The skin, liver, and small intestine were removed and fixed in 10% buffered formalin. The fixed tissue was embedded in paraffin, sections were prepared and stained with hematoxylin/eosin, and then observations were made under an optical microscope. Histologic changes thought to correspond to GVHD in typical organs were as follows: skin (mononuclear infiltration into the dermoepidermal junction, and damage to hair follicles or sebaceous glands); liver (periportal mononuclear infiltration and hepatocellular necrosis); and small intestine (apoptosis of crypt cells and dilatation or flattening of the villi). For each of these changes in the organs the scoring system assigned a score of zero for negative findings and a score of 1 for positive findings (the maximum possible score for each mouse was 6). FIG. 1 shows the average pathology score at each time point together with the observed clinical signs. These results were typical throughout 5 independent studies. The recipient mice have pathological signs of GVHD at all post-transplantation time points, and the pathology score was highest on day 14. The pathology score matched the clinical findings for GVHD at each time point.

Plasma Samples

Blood samples were taken before BMT and on days 7, 14, 21, and 28 after BMT. The blood samples were collected using a heparin-coated capillary tube from the caudal veins of living mice, and centrifuged at 10,000 rpm for 5 min within 30 min to prepare plasma. The plasma samples were stored at −80° C. until assay.

Example 2

SELDI Protein Chip Array Analysis

To 10 µL of each plasma sample was added 20 µL of a solution comprising 9 mol/L urea and 10 g/L CHAPS in Tris-HCl (pH 7.4). The mixture was mixed for 15 min at 4° C. with a vortex mixer, and was then diluted to 1:40 in Tris-HCl. Eight-spot immobilized metal affinity capture arrays (IMAC-30) were activated with 50 mmol/L $CuSo_4$. Diluted samples (50 µL) were applied to each spot of the protein chip array, and incubated for 1 h on a shaker. After washed with the same Tris-HCl, the chip was gently rinsed with water, and 0.5 µL of saturated sinapinic acid (SPA) was applied twice to each spot, and then air-dried. The mass/charge (m/z) spectra of the proteins bound to the chelated metal were measured using a Ciphergen Protein Biology System II Time-Of-Flight mass spectrometer (PBS II, Ciphergen Biosystems, Inc.) The data were calculated by averaging 65 laser shots obtained at a laser intensity of 200 and a detector sensitivity of 8.

Statistical Analysis of SELDI-TOF MS

All spectra were compiled and the data was preliminary analyzed using Ciphergen Protein Chip Software 3.2.0. For the plasma samples, 50 samples from the GVHD group (post-transplantation days 7, 14, 21, and 28) and 28 samples from the control group (before BMT) were used for a total of 78 samples. A total of 169 peaks that appeared to differ were detected in the range of m/z=2 k to 200 k. When peaks with a change in intensity of 5-fold or greater and a level of significance of p<0.05 were extracted by making a comparison between the two groups using Biomarker Pattern's Software, in the GVHD group there were 10 peaks that were higher and 9 peaks that were lower than in the control.

Protein Profiling by SELDI-TOF MS

The 169 peaks in the above mass range of 2.0 to 200 kDa was further analyzed using the peak intensity values. A classification tree was developed with Biomarker Pattern's Software (BPS, Ciphergen Biosystems, Inc.) using all 169 peaks by a cross variation procedure. Simply put, in a classification tree the data are split into two nodes using one rule at a time in the form of a question. In this study the splitting decisions were made based on the normalized intensity level of peaks or clusters identified from the SELDI protein expression profile. In other words, each peak or cluster identified from the SELDI profile becomes a variable in the classification process. The splitting process was continued until terminal nodes were reached and further splitting yielded no gain in data classification.

A plurality of classification trees were generated using this process, and the best performing tree was selected based on classification tree analysis. As a result, a peak at 8972 Da was selected as one peak that was significantly higher in the GVHD group than in the control group. The 8972 Da peak provided differentiation of the GVHD group and the control group at 100% both in terms of sensitivity and specificity.

Figure 2:
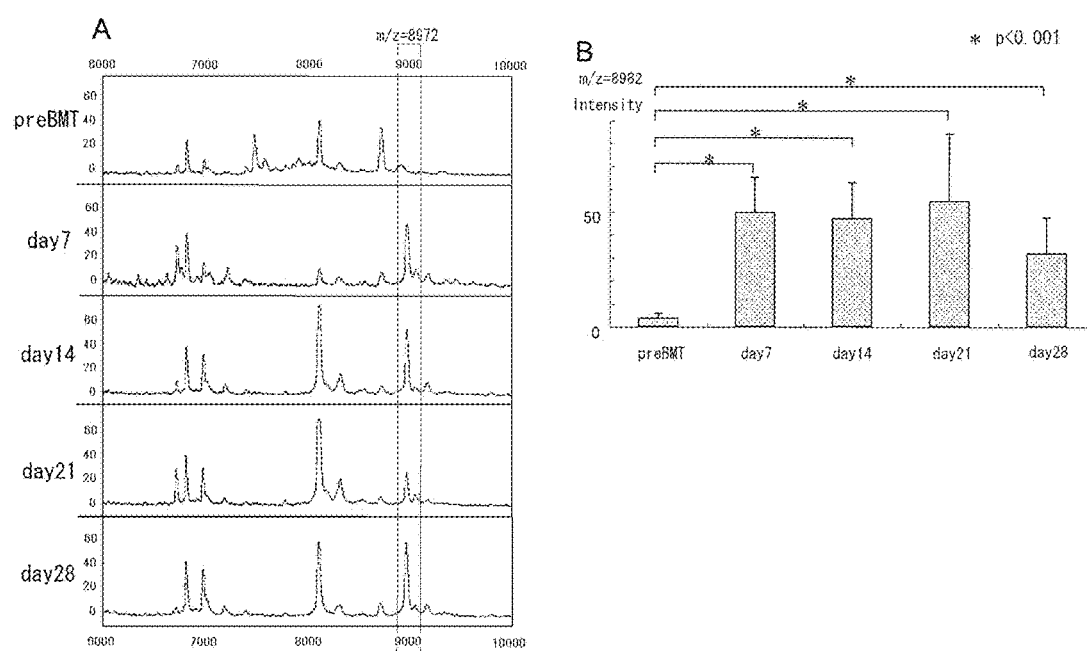
FIGS. 2A-B show a typical SELDI spectrum from a sample obtained from a GVHD model mouse (A) and the average normalized intensity of the 8972 Da peak in the sample at each time point (B)

FIG. 2 shows an example of the 8972 Da peak. FIG. 2A shows representative SELDI spectra from a normal control sample (pre-BMT, pre-transplantation) and GVHD sample (post-transplantation days 7, 14, 21, and 28) obtained from the same individual at a range from 6000 to 10,000 Da. The part surrounded by the line shows a peak with an average mass of 8972 Da. This peak is overexpressed in GVHD plasma compared with normal plasma, and the peak intensity on day 7 and beyond was significantly higher than in the control. Both the tissue score and peak intensity decreased on day 28. FIG. 2B shows the average normalized intensity values of the 8972 Da peak in samples at various time points (n=9 at each point). The average expression of the peak in the GVHD sample was significantly higher than the average expression in the control sample (pre-BMT, pre-transplantation).

CsA Treatment Model

Figure 3:
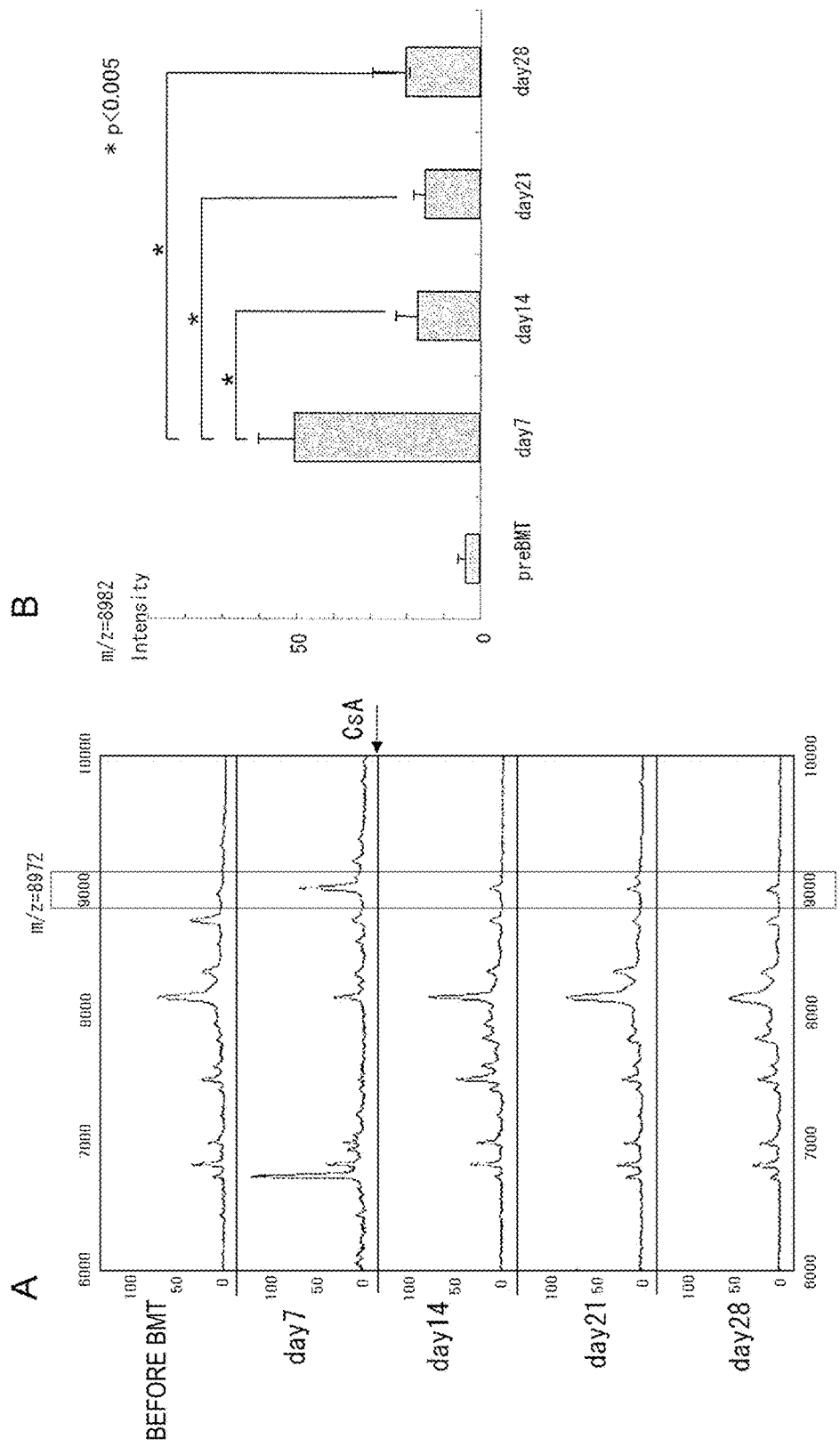
FIGS. 3A-B show a representative SELDI spectrum from a sample obtained from a model mouse receiving cyclosporin-A (CsA) (A), and the average normalized intensity of the 8972 Da peak in the sample at each time point (B)

Cyclosporin-A (CsA) (Novartis Pharma), a therapeutic drug for GVHD, was diluted to 1.67 mg/mL in a 0.9% NaCl solution. CsA was administered intraperitoneally at a dose of 20 mg/kg daily from post-transplantation day 8 through day 13. FIG. 3 shows the change in the 8972 Da peak in the same individuals treated with CsA, and the average normalized intensity value of the 8972 Da peak in the sample at each time point (n=4 at each point). In the GVHD mice treated with CsA, the 8972 Da peak intensity was high on day 7, and then dropped after the administration of CsA.

Syngeneic Transplantation Model

Figure 4:
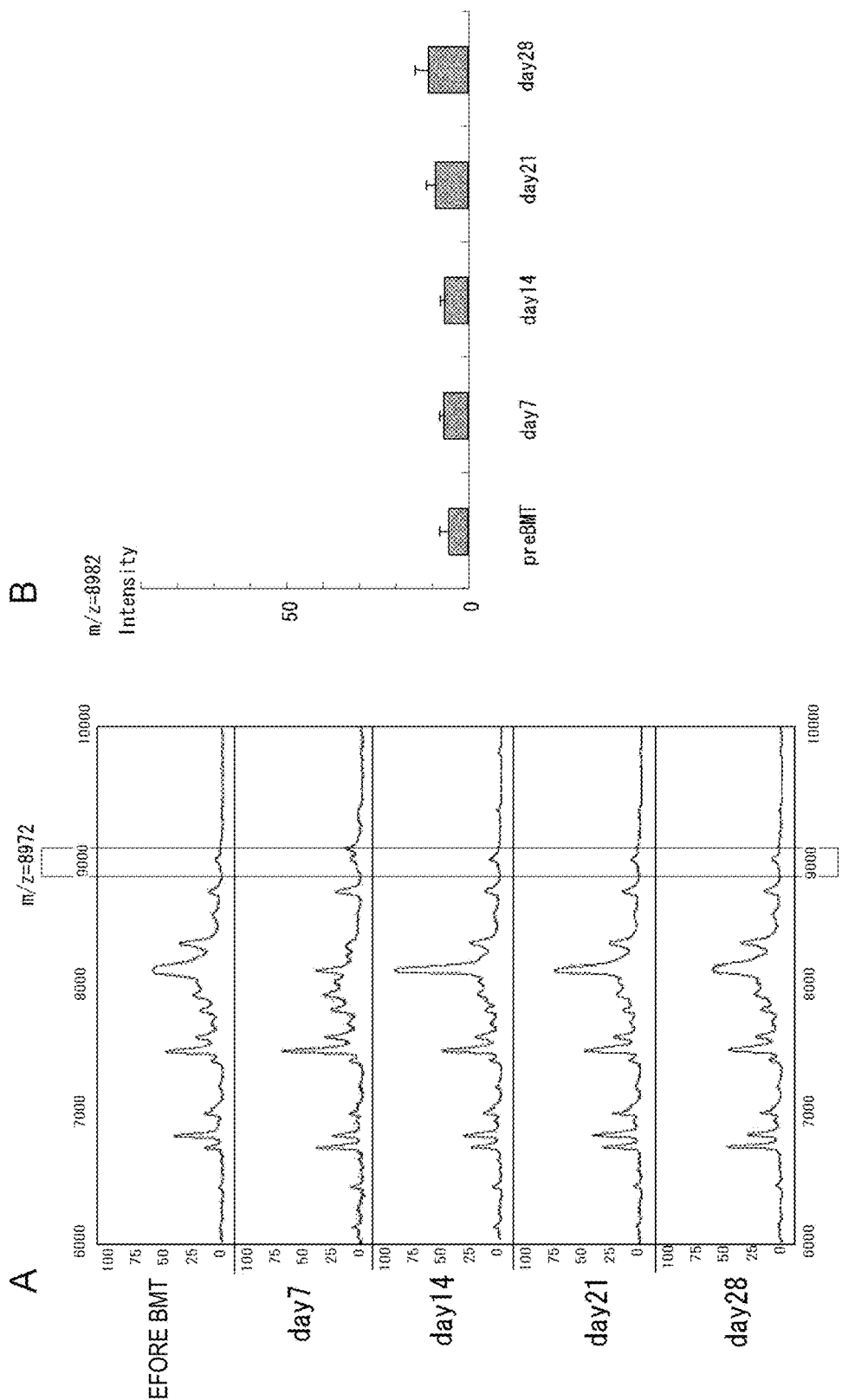
FIGS. 4A-B show a representative SELDI spectrum from a sample obtained from an syngeneic transplant model mouse (A), and the average normalized intensity of the 8972 Da peak in the sample at each time point (B)

In an syngeneic transplantation model using BALB/c mice with a bone marrow graft transplanted from a BALB/c mouse, GVHD was not induced, and no significant difference in average peak expression was found between pre-transplantation and post-transplantation samples (FIGS. 4A and 4B).

Example 3

Separation of Proteins

The three most abundant proteins in the plasma (albumin, IgG, transferrin) were removed from the pooled plasma sample by immunodepletion chromatography (Multiple Affinity Removal Column MS-3, 4.6 mm ID×50 mm; Agilent). A 5-fold dilution of 50 µL of plasma in Buffer A (Agilent) was prepared and injected into the immunodepletion column. The flow-through fractions were collected and further separated by high-performance liquid chromatography (HPLC). The separation column used in HPLC was an Inertsil™ Ph column (5 µm, 4.6 mm ID×150 mm; GL Sciences, Japan). The elution gradient profile was as follows: (1) Elution solvent A: 2% ACN/0.1% TFA, solvent B: 80% ACN/0.1% TFA; (2) Linear gradient: 0 to 100% for solvent B for 50 min; flow rate 1.0 mL/min.

Figure 5:
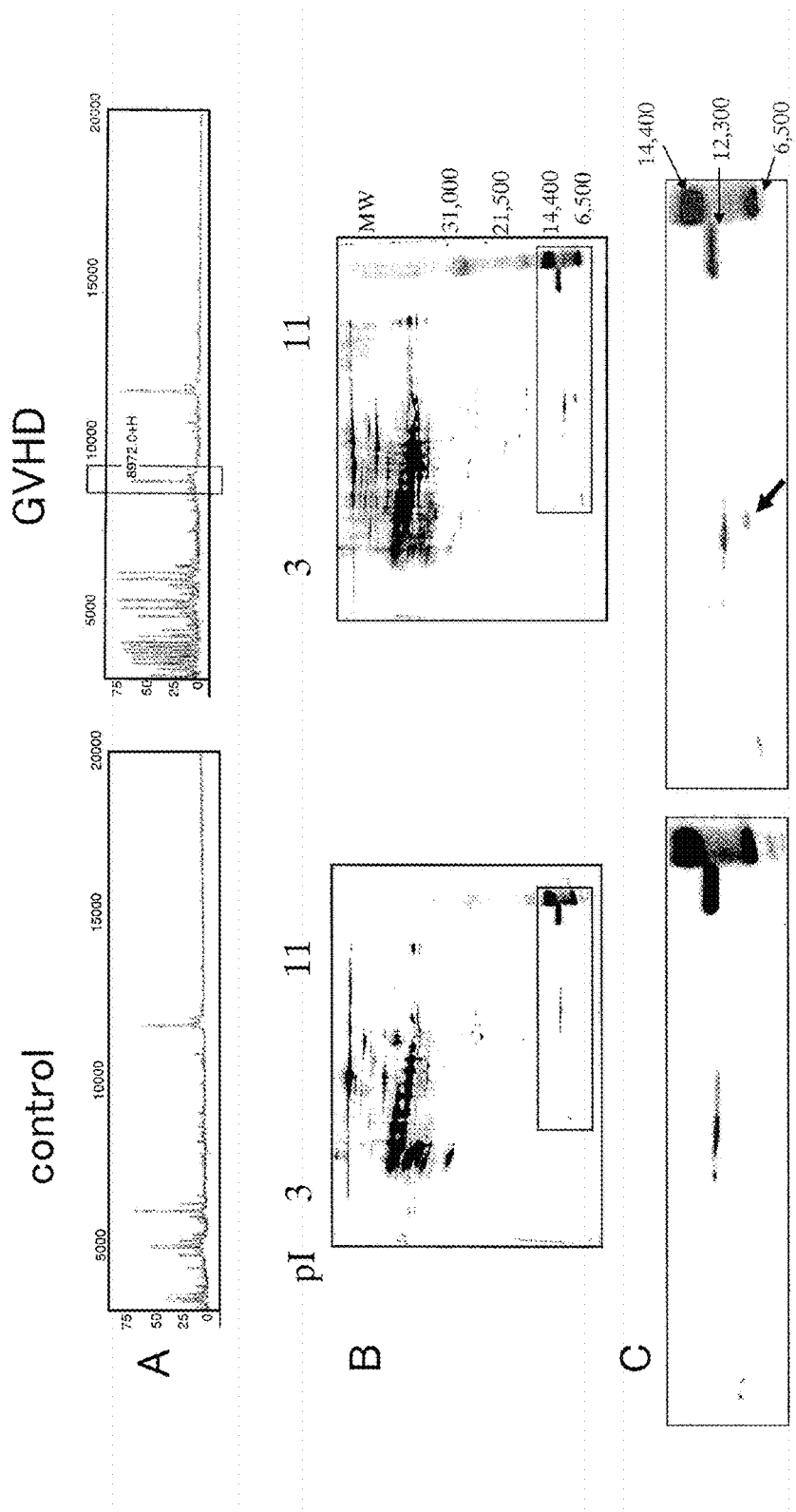
FIGS. 5A-C show the SELDI spectrum of the HPLC fraction containing the 8972 Da protein (A) and the results of two-dimensional electrophoresis (B and C)

The fractions were collected at 30 sec intervals, 2 µL of each fraction was applied to an Au chip (Cipheragen), processed with an SPA matrix, and the composition of each fraction was monitored by SELDI-TOF MS. The HPLC fraction from 31.0 to 31.5 min (approximately 38% acetonitrile) was collected based on SELDI-TOF MS monitoring. A large amount of the 8972 Da protein was contained in the GVHD sample, but almost none was present in the control sample (FIG. 5A). This fraction was lyophilized and dissolved in 200 µL of solubilization buffer (7 M urea, 2 M thiourea, 50 mM DTT, 2 µL ampholine, 3% CHAPS, 1% Triton X-100).

Next, the sample concentrated in that manner was separated with two-dimensional electrophoresis. After sonication the sample solutions were loaded onto IPG gel strips (pH 3-11, NL, 11 cm long, Amersham Bioscience), and the strips were rehydrated for 10 hours at 30 V. The first-dimensional separation by isoelectric focusing (IEF) was performed at 20° C. for a total of 12 kV/hr using the IPGphor system (Amersham Bioscience). After IEF, the IPG strips were equilibrated for 15 min in 50 mM Tris-HCl (pH 8.8) containing 6 M urea, 2% SDS, 30% glycerol, 0.002% bromophenol blue, and 1% dithiothreitol. Next, the strips were equilibrated for 15 min in the same buffer except 2.5% iodoacetamide replaced the dithiothreitol. For the second-dimensional separation, SDS-PAGE was performed using a polyacrylamide gel with an 8 to 20% gradient at a constant current of 40 mA/gel. After two-dimensional electrophoresis, the proteins were made visible by silver nitrate staining. By comparing the images of the two gels from the GVHD and control samples, a spot located at 6,500 Da to 12,300 Da was identified that was highly expressed in the GVHD sample (FIGS. 5B and 5C).

Protein Identification

The spot of the 8972 Da candidate protein was digested in the gel. In short, the gel spot was cut out and washed with 100% ACN and 100 mM NH$_4$HCO$_3$, vacuum dried, and incubated at 37° C. for 16 hours in 5 µL of trypsin solution (12.5 ng/µL in 50 mM NH$_4$HCO$_3$ and 5 mM CaCl$_2$). The resulting peptides were extracted once in 20 µL of 20 mM NH$_4$HCO$_3$ and three times in 20 µL of 5% formic acid in 50% ACN. The collected extracts were vacuum dried to approximately 40 µL, and analyzed by nanoflow HPLC-ESI-MS/MS. For HPLC a DiNa system (KYA Technology) was used, and the trypsin-digested samples were separated on a HIQsil™ C18 column (75 µm ID×50 mm; KYA Technology). The separation conditions were as follows: Elution solvent A: 0.1% formic acid, solvent B: 0.1% formic acid in 70% ACN; gradient: 0 to 100% for solvent B for 40 min; flow rate: 200 nL/min. The properties of the separated peptides were determined using a QSTAR XL Q-TOF mass spectrometer (Applied Biosystems). A search of the NCBI protein database was performed with MASCOT software (Matrix Science Inc.) using the obtained mass spectral data.

Figure 6:
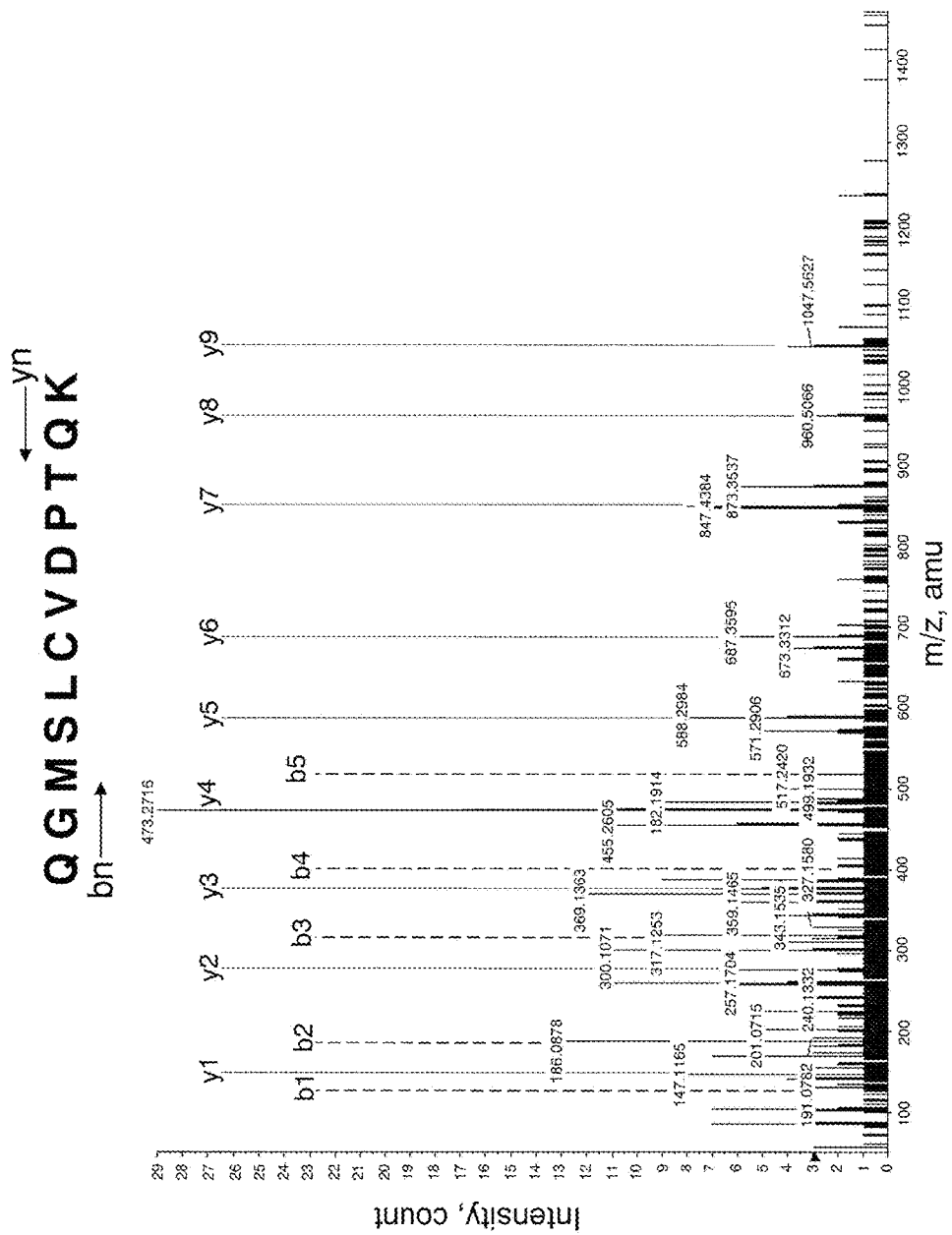
FIG. 6 shows a representative MS/MS spectrum of the peptide derived from the 8972 Da protein and the amino acid sequence identified.

The result of the search showed that a partial amino acid sequence of the 8972 Da protein matched the sequence of a CCL8 precursor. FIG. 6 shows a typical MS/MS spectrum of a peptide separated from the 8972 Da protein. This peptide was identified by nano LC-MS/MS as CCL8 peptide 68-79 (QGMSLCVDPTQK). Similarly, 11 peptides were identified that matched the theoretical mass. When these peptide sequences were combined, 52% of the amino acid sequence of the CCL8 precursor was covered (underlines).

```
                                                         (SEQ ID NO: 1)
 1    MKIYAVLLCL LLIAVPVSPE KLTGPDKAPV TCCFHVLKLK IPLRVLKSYE

51    RINNIQCPME AVVFQTKQGM SLCVDPTQKW VSEYMEILDQ KSQILQP
```

The predicted mass of the CCL8 precursor is 11,017 Da, and the predicted pI is 8.64. The CCL8 precursor contains a signal peptide of 19 amino acids followed by a mature CCL8 sequence of 78 amino acid residues. The predicted mass of the mature CCL8 is 8972 Da, and the predicted pI is 8.45. These numbers are consistent with the data obtained by SELDI-TOF MS and two-dimensional electrophoresis (2D-PAGE).

Example 4

Verification of CCL8 Expression by Immunoassay

Figure 7:
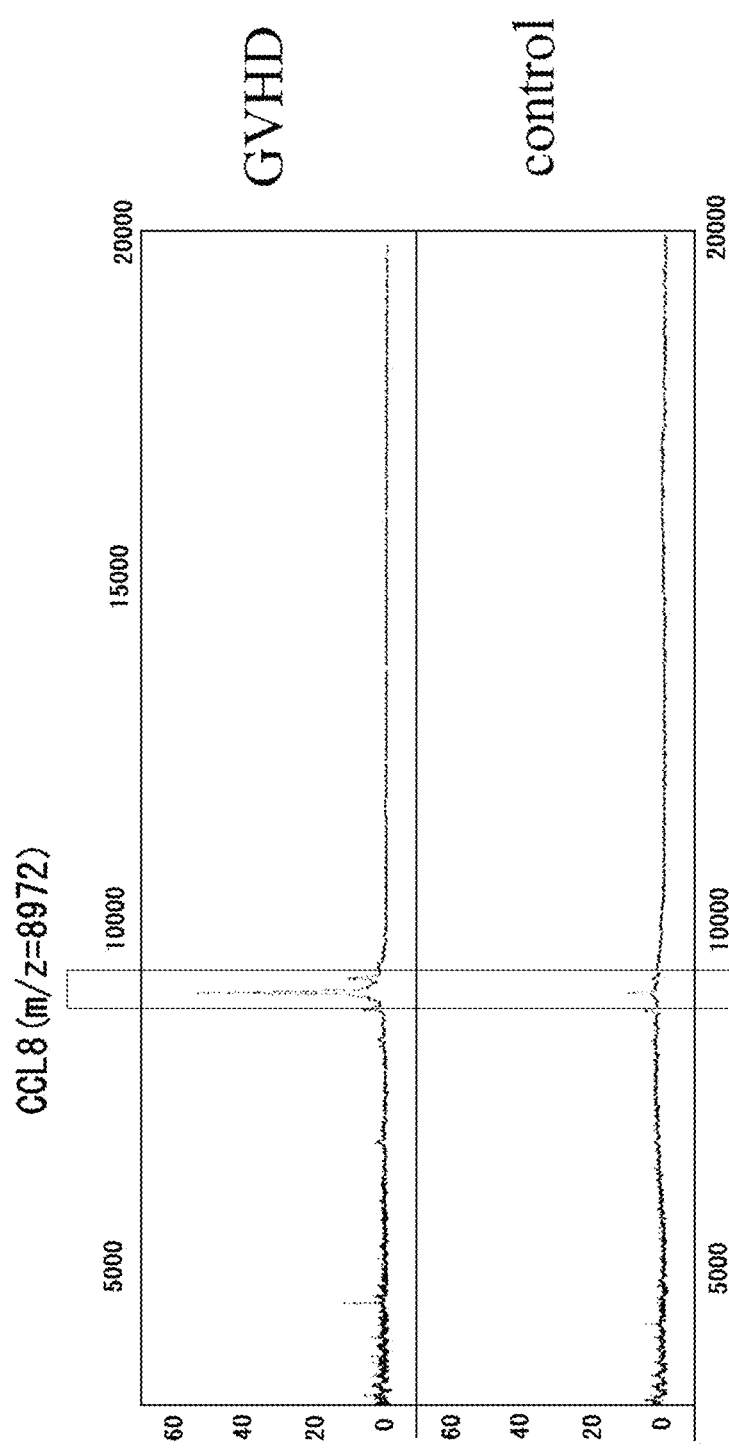
FIG. 7 shows the detection of the CCL8 protein by immunoassay.

The fact that the 8972 Da marker is CCL8 was verified by SELDI immunoassay using a specific anti-mouse CCL8 rabbit antibody. To each spot on a PS20 (preactivated surface) ProteinChip (Ciphergen Biosystems) was added 0.1 µg of anti-mouse CCL8 antibody, and the chip was incubated for 2 hours at room temperature in a humidified chamber. After the residual active sites were blocked for 30 min with 5 µL of 1M ethanolamine (pH 8.0), the spots were washed three times with 0.5% Triton X-100 in PBS and twice with PBS. The plasma sample was diluted 1:75 in PBS, applied to the antibody-immobilized spots on the PS20 chip, and incubated for 2 hours with gentle mixing at room temperature using a bioprocessor. Each spot was washed twice with 0.5% Triton X-100 in PBS and twice with PBS. After a brief wash with 5 mM HEPES, SPA matrix was added, and MS analysis was performed using a PBS II ProteinChip reader. CCL8 was detected in the GVHD plasma sample, but was only barely detected in the control sample (FIG. 7).

Example 5

CCL8 Expression in Human Clinical Samples

Plasma obtained from patients that had undergone bone marrow transplantation was diluted 1:25 in PBS and used for human clinical samples. As in Example 4, a PS20 ProteinChip was used together with an anti-human CCL8 antibody to investigate the expression of CCL8 in human patients by SELDI immunoassay.

Patient 1 (FIG. 8)
Five-year-old male
Diagnosis: Fanconi anemia
Treatment: Umbilical cord blood stem cell transplantation from unrelated donor (CBSCT (UR))
Prophylaxis: CsA+MMF
Course: GVHD first developed on post-transplantation day 13 with a skin rash, and methylprednisolone (mPSL) therapy was started the same day. CCL8 was detected on post-transplantation day 10 before the clinical manifestation of GVHD. The level of CCL8 temporarily decreased with this treatment. However, the amount of CCL8 expression rose once again together with the recurrence of GVHD. The patient had responded to treatment at first, but ultimately died due to treatment-resistant GVHD. The amount of CCL8 expression correlated with the development of GVHD and therapeutic efficacy. The level of CCL8 no longer fell after resistance to therapy developed.

Patient 2 (FIG. 9)
Ten-year-old male
Diagnosis: Chronic myelogenous leukemia (CML)
Treatment: Bone marrow transplantation from unrelated donor (BMT (UR))
Prophylaxis: FK+MTX
Course: GVHD first developed on post-transplantation day 19 with a skin rash, and methylprednisolone (mPSL) therapy was started the same day. On that day the level of CCL8 showed a clear increase. The GVHD progressed temporarily from stage 2 to stage 3, but improved with therapy, and a high level of CCL8 expression was not found thereafter.

Figure 10:
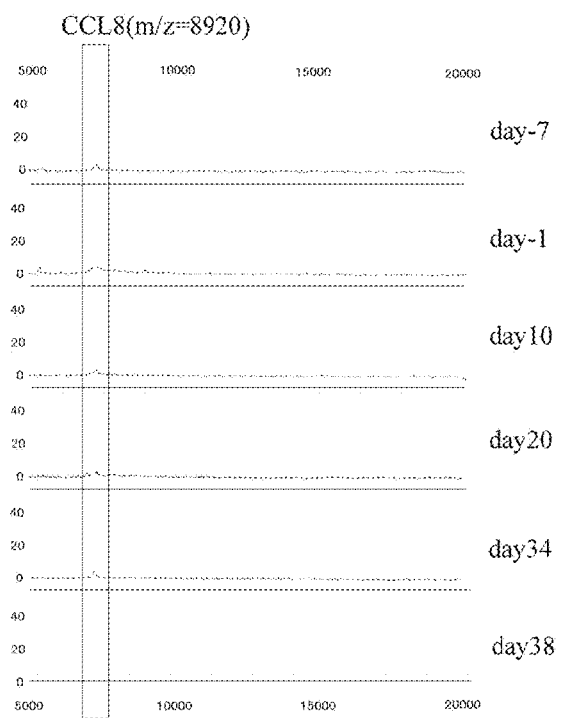
FIG. 10 shows the detection of the CCL8 protein in a human clinical sample.

Patient 3 (FIG. 10)
Three-year-old female
Diagnosis: Acute lymphoblastic leukemia (ALL)
Treatment: Bone marrow transplantation from matched sibling (BMT (matched-sib.))
Prophylaxis: MTX
Course: GVHD did not develop. No elevation of CCL8 expression was found at any time throughout the course.

Figure 12:
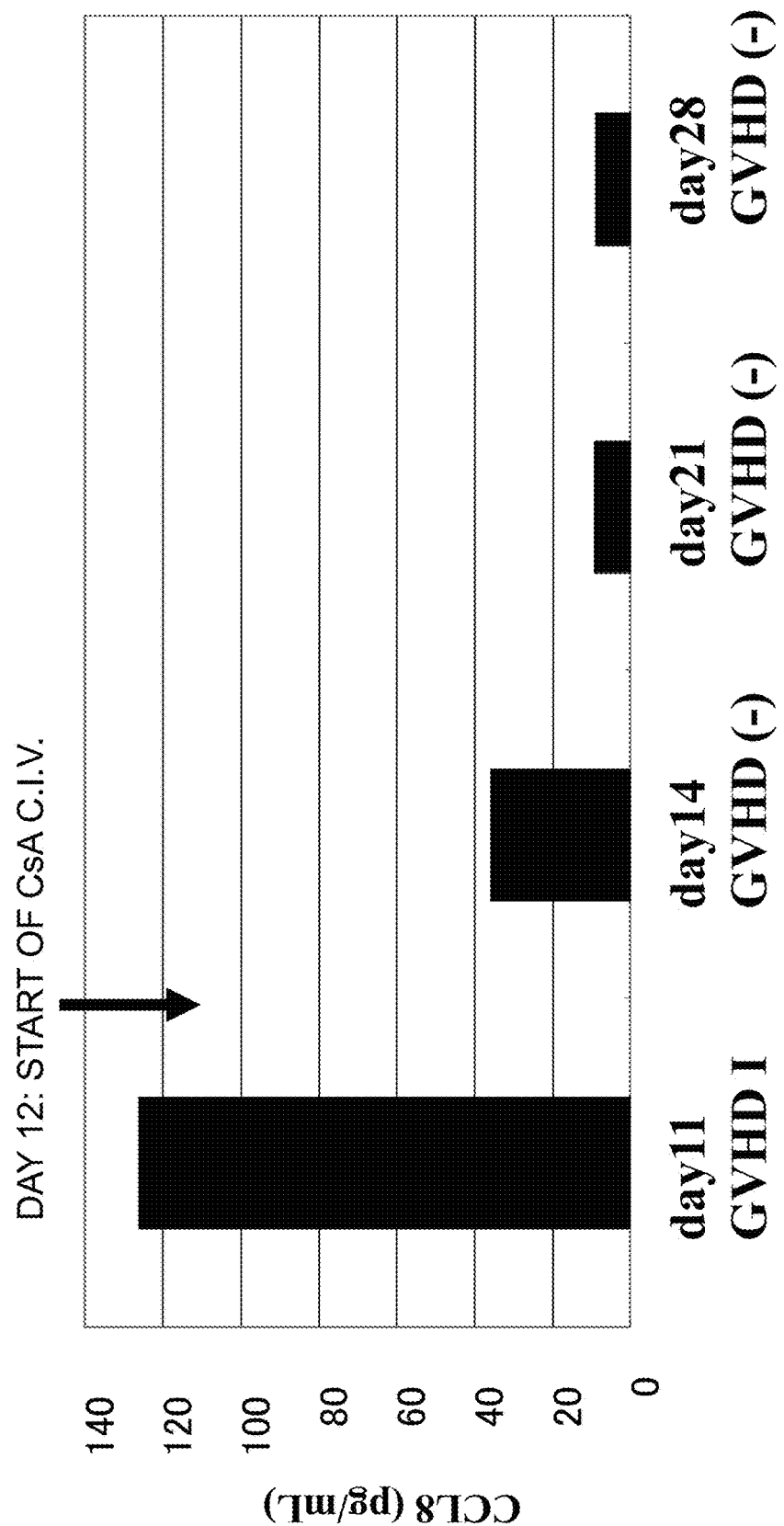
FIG. 12 shows the time course of the CCL8 protein level in a human clinical sample.

Patient 4 (FIG. 12)
Eleven-year-old female
Diagnosis: Acute lymphoblastic leukemia (ALL)
Treatment: Bone marrow transplantation from matched sibling donor (MSD-BMT)
Prophylaxis: Short-term MTX
Course: GVHD developed on post-transplantation day 11. The level of CCL8 expression showed an increase. On the same day cyclosporin-A was administered by continuous intravenous infusion (C.I.V.). On day 14 the symptoms of GVHD had improved, and the level of CCL8 expression had fallen.

Figure 13:
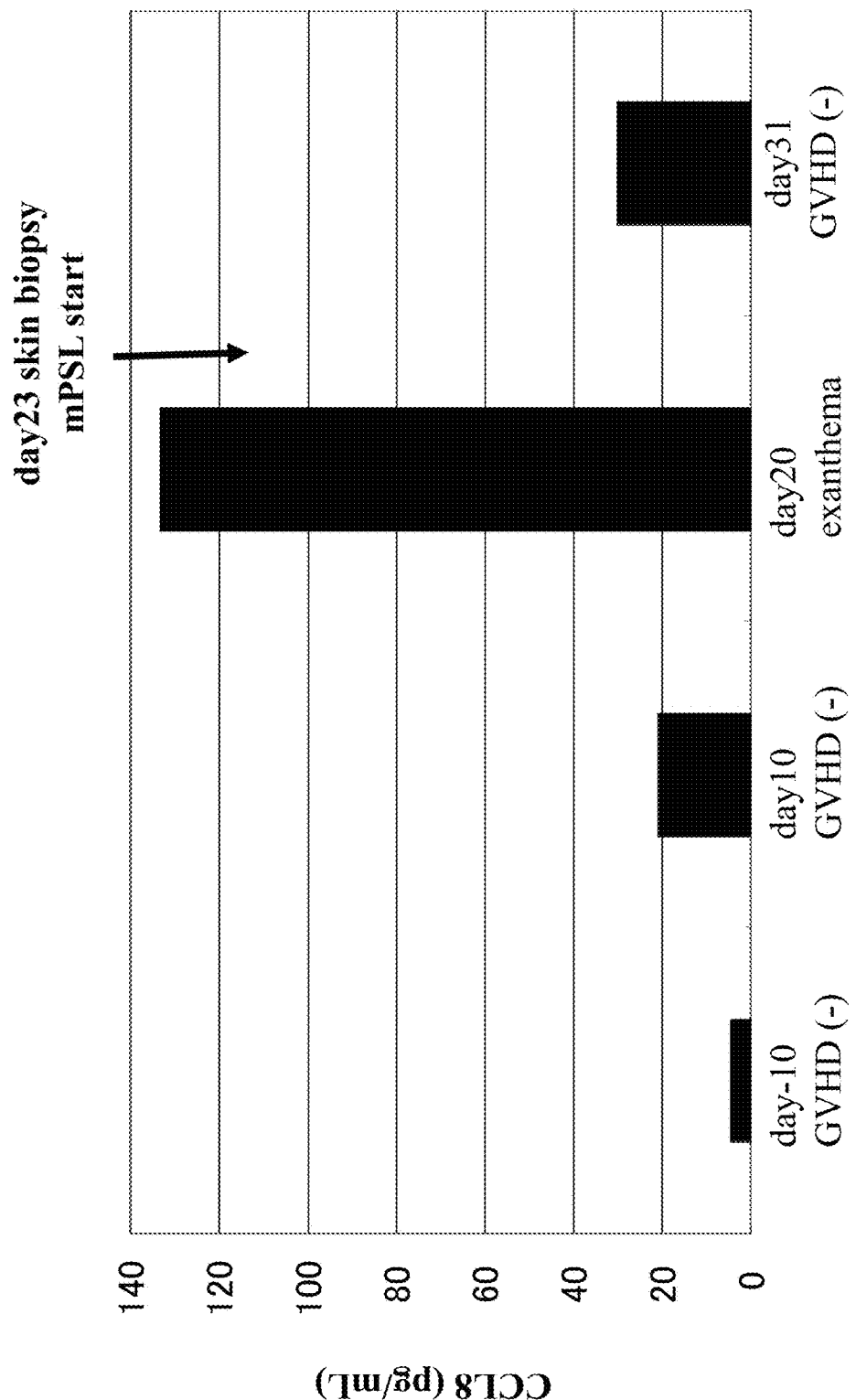
FIG. 13 shows the time course of the CCL8 protein level in a human clinical sample.

Patient 5 (FIG. 13)
A 19-year-old female with severe aplastic anemia underwent bone marrow stem cell transplantation from a parent without a matching HLA-1 antigen. The patient underwent pre-transplantation conditioning consisting of 150 mg/m$^2$ fludarabine (Flu), 120 mg/kg cyclophosphamide (CY), and 24 mg/kg anti-thymocyte globulin (ATG), and prophylaxis for GVHD with tacrolimus. On day 10, the patient developed a high fever, and on day 16 an atypical skin rash appeared on the limbs and trunk, but without diarrhea. On day 20 the level of CCL8 showed a clear increase. On day 23 a skin rash biopsy was performed, and methylprednisolone (mPSL) therapy was started. On day 31 the symptoms of GVHD had improved, and the level of CCL8 expression had fallen.

Example 6

CCL8 Plasma Concentration in GVHD Patients and Normal Individuals

The amount of CCL8 was quantified in the plasma of normal individuals, and among post-HSCT patients, in the plasma of those who developed GVHD and those who did not. FIG. 11 shows the results. The numerical units are pg/mL. In patients that had undergone HSCT, the CCL8 plasma concentration in those who did not develop GVHD was 6.92 to 48.0 pg/mL, and the mean was 23.3 pg/mL. The CCL8 plasma concentration in those who did develop GVHD was 52.0 to 333.6 pg/mL, and the mean was 133.3 pg/mL, which was clearly a higher concentration. Furthermore, in the two treatment-resistant GVHD cases the concentrations were 333.6 pg/mL and 290.4 pg/mL, which were extremely high concentrations. These two patients were resistant to GVHD therapy and died. In normal individuals the CCL8 plasma concentration was 0 to 32.6 pg/mL and the mean was 18.9 pg/mL, which was an extremely low value. From these findings it was learned that the amount of CCL8 in the plasma of patients who developed GVHD was significantly higher than in normal individuals, and in treatment-resistant GVHD patients, it was dramatically higher.

The above results clearly indicate that there is a strong correlation between the amount of CCL8 expression and the development and course of GVHD in human patients.

Example 7

Infection and Differential Diagnosis

The level of CCL8 expression was measured in mice administered a TLR ligand.

Male BALB/c (H-2$^d$) mice were purchased from Sankyo Labo Service Corporation (Tokyo, Japan). The mice were 8 to 10 weeks old at the start of testing. Unless otherwise indicated, all reagents were purchased from SIGMA/ALDRICH (Tokyo, Japan).

Wild type BALB/c mice were given an intraperitoneal injection of 5 µg lipopolysaccharide (LPS) (*Escherichia coli*), 5 µg of poly(I:C) (GE Healthcare Bio-sciences, Tokyo, Japan), and 20 mg of D-GalN, 100 mg of peptide glycan (PGN (*Staphylococcus aureus*)) (Invitrogen, CA, USA), 20 mg of Zymosan-A (Invitrogen, CA, USA), and 20 nmol Cpg-ODN (Invitrogen, CA, USA) in 500 µL of PBS. The control mice were given an intraperitoneal injection of 500 of PBS. Four hours after the injection, a plasma sample was collected. The doses of LPS, poly(I:C), PGN, Zymosan-A, and CpG-ODN were determined by preliminary experiments.

Four hours after the injection, the mouse blood was sampled using a heparin-coated syringe, and centrifugal separation was performed on the blood for 7 min at 5000 rpm within 30 min of sampling to obtain plasma. The divided plasma samples were stored at −80° C. until assay. Blood samples were collected from human volunteers and patients, plasma samples were prepared, and those divided samples were stored at −80° C. until assay.

The human CCL8 was measured by enzyme-linked immunosorbent assay (ELISA). An ELISA kit for human CCL8 was purchased from RayBiotech (Norcross, Ga.), and the manufacturer's protocol was followed. The plates were read with a plate reader at 450 nm (Multiskan JX, Thermo Labsystems, Helsinki, Finland).

The results were expressed as mean±S.E. A statistical analysis for significance was performed using either a two-tailed or one-tailed t-test. The level of significance was set at $p<0.05$. A Bonferroni correction for multiple comparisons was used. The results shown are representative data for a series of tests.

As shown in FIG. 14, it is clearly demonstrated that the level of CCL8 does not increase by the administration of TLR ligand. This finding shows that the level of CCL8 expression does not increase by bacterial or viral infection, and indicates that differential diagnosis between GVHD and infection may be effected by using CCL8 expression as an indicator.

Example 8

Diagnosis Before Manifestation of GVHD

As in Example 1 syngeneic BMT was performed in mice, blood was collected on post-transplantation days 1, 3, 5, and 7, and heparin-plasma samples were obtained. The concentration of CCL8 in the plasma was quantified using ELISA for mouse CCL8.

Change in weight from syngeneic BMT post-transplantation day 0 to 7 and weight loss, hunched posture, coat, skin, and diarrhea on day 7 were evaluated on a 3-step scale of 0, 1, or 2 points. A score of 0 was assigned to a weight loss of <10%; score of 1 to a weight loss of 10% to <25%; and score of 2 to a weight loss of ≥25%. For hunched posture, a score of 0 was assigned to a normal posture; score of 1 to a slightly hunched posture; and score of 2 to a very hunched posture. For coat, a score of 0 was assigned to normal; a score of 1 to slightly ruffled fur; and a score of 2 to whole body ruffled fur with almost no grooming. For skin, a score of 0 was assigned to normal skin; a score of 1 to visible sclerosis on the tail and legs; and a score of 2 to mice with patchy alopecia. For diarrhea, a score of 0 was assigned to normal; a score of 1 to slight diarrhea; and a score of 2 to full-blown diarrhea. The clinical GVHD score represents the total number of points for each criterion, and the maximum number of points is 10.

Figure 15:
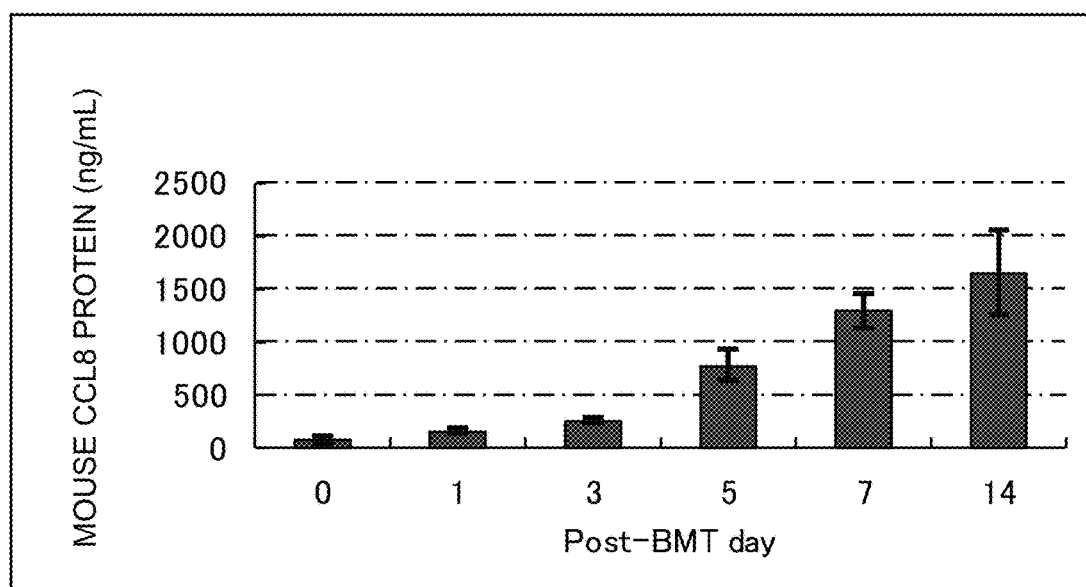
FIG. 15 shows the time course of the clinical signs and in the level of CCL8 protein in a GVHD model mouse.

FIG. 15 shows the time-course changes in CCL8 plasma concentration. The CCL8 plasma concentration increased soon after bone marrow transplantation and was markedly higher after day 5. In contrast, until day 6 no clinical manifestations of GVHD were observed. The clinical evaluation of GVHD was approximately 2.5 points on day 7, which represents early-stage GVHD. Thereafter, the GVHD signs progressed in all mice starting on day 7, and the score on day 28 was 6.3.

Based on these findings it is believed that the quantitation of the CCL8 protein in the blood is useful for the pre-clinical or early stage diagnosis of GVHD in mice.

Example 9

Treatment of GVHD with Anti-CCL8 Antibody

An anti-mouse CCL8 rabbit antibody was prepared by administering a synthesized CCL8 peptide to a rabbit, and purifying the anti-CCL8 IgG fraction from the resulting antiserum using an affinity column. An IgG fraction from the serum of a normal rabbit was used as a normal rabbit antibody control.

Bone marrow transplantation was performed on mice as in Example 1. Anti-mouse CCL8 rabbit antibody or normal rabbit antibody was administered in a dose of 100 μg to the recipient mouse via the caudal vein for 3 consecutive days counting from the day before allogeneic BMT. Three mice each were treated with anti-mouse CCL8 antibody (treatment group) and normal rabbit antibody (control group). On post-BMT day 14 the mice were sacrificed by cervical dislocation. The skin, liver and small intestine were removed and fixed in 10% buffered formalin. The fixed tissue was embedded in paraffin, sections were prepared and stained with hematoxylin/eosin, and then observations were made under an optical microscope to look for pathological signs considered indicative of GVHD. The scoring method was as follows: skin (infiltration of monocytes into the dermoepidermal junction, and damage to follicles or sebaceous glands); liver (periportal mononuclear infiltration and hepatocellular necrosis); and small intestine (apoptosis of crypt cells and dilatation or flattening of villi). Findings were given an interpretation of positive (+), intermediate (+/−), or negative (−) on a 3-step scale.

Figure 16:
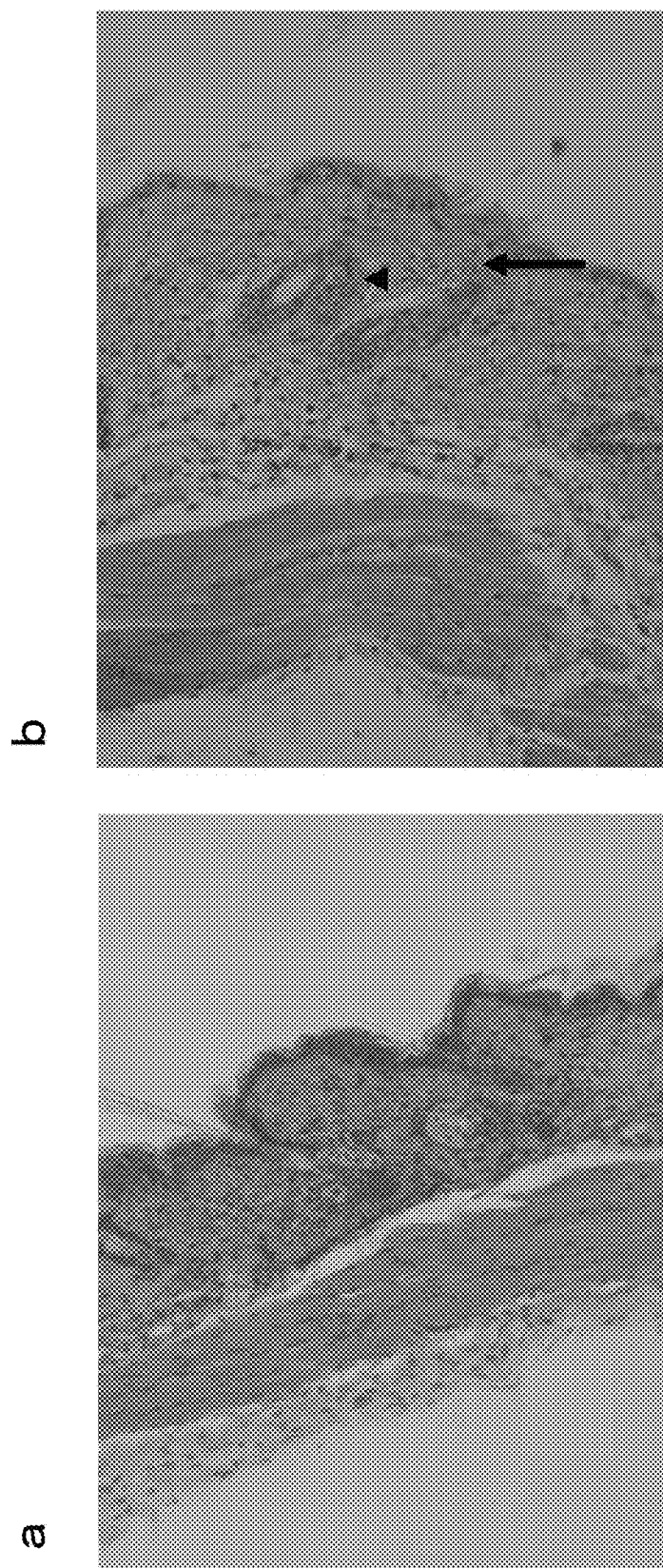
FIGS. 16a-b show histochemical staining of a GVHD model mouse receiving an anti-CCL8 antibody (a) or a normal rabbit antibody (control) (b)

A typical image of stained skin tissue is shown in FIG. 16, with (a) showing the administration of the anti-mouse CCL8 antibody and (b) showing administration of the normal rabbit antibody (control). Damage (arrowhead) to the sebaceous glands and lymphocyte infiltration (arrow) into the dermoepidermal junction, which are signs of GVHD in skin, can be seen in the group administered normal rabbit antibody, but these are not found in the group administered the anti-mouse CCL8 antibody.

FIG. 17 shows the results using the above scoring system. A decrease in inflammatory cell infiltration into the dermoepidermal junction and amelioration of damage to hair follicles and sebaceous glands in the skin were seen only in the mice treated with the anti-CCL8 antibody. This finding indicates that treatment with an anti-CCL8 antibody is effective in the treatment of GVHD.

INDUSTRIAL APPLICABILITY

The present invention is useful for the diagnosis, course monitoring, and treatment of GVHD.

The invention claimed is:

1. A method of treating acute graft-versus-host disease (GVHD) in a human subject who has been treated with a hematopoietic stem cell transplant, the method comprising:
   (a) measuring or obtaining results of measurements of the level of CCL8 protein in a first sample obtained from the human subject at a first time point and in a second sample obtained from the human subject at a second, later time point; and
   (b) initiating therapy for acute GVHD when the level of CCL8 protein in the second sample is increased, by administering an anti-CCL8 antibody to the human subject.

2. The method of claim 1, further comprising:
   (c) measuring the level of CCL8 protein in a third sample obtained from said human subject at a time point after the therapy, or obtaining the result of a measurement of CCL8 protein in the third sample; and
   (d) evaluating the therapeutic effect for the acute GVHD therapy based on the level of CCL8 protein in the third sample.

3. The method according to claim 1, wherein the human subject is not yet showing any clinical manifestations of acute GVHD.

4. The method according to claim 1, wherein in step (b), the therapy for acute GVHD is initiated before clinical manifestations of acute GVHD in the human subject.

5. The method according to claim 1, wherein the level of CCL8 protein is measured using an anti-CCL8 antibody.

6. The method according to claim 1, wherein the level of CCL8 protein is measured using a method selected from mass spectrometry, high-performance liquid chromatography, and two-dimensional electrophoresis.

7. A method for treating acute graft-versus-host disease (GVHD), comprising administering an anti-CCL8 antibody to a subject suffering from acute GVHD.

* * * * *

SEQUENCE LISTING

<160> NUMBER OF SEQ ID NOS: 2

<210> SEQ ID NO 1
<211> LENGTH: 97
<212> TYPE: PRT
<213> ORGANISM: homo sapiens

```
<400> SEQUENCE: 1

Met Lys Ile Tyr Ala Val Leu Leu Cys Leu Leu Leu Ile Ala Val Pro
1               5                   10                  15

Val Ser Pro Glu Lys Leu Thr Gly Pro Asp Lys Ala Pro Val Thr Cys
            20                  25                  30

Cys Phe His Val Leu Lys Leu Lys Ile Pro Leu Arg Val Leu Lys Ser
        35                  40                  45

Tyr Glu Arg Ile Asn Asn Ile Gln Cys Pro Met Glu Ala Val Val Phe
    50                  55                  60

Gln Thr Lys Gln Gly Met Ser Leu Cys Val Asp Pro Thr Gln Lys Trp
65                  70                  75                  80

Val Ser Glu Tyr Met Glu Ile Leu Asp Gln Lys Ser Gln Ile Leu Gln
                85                  90                  95

Pro

<210> SEQ ID NO 2
<211> LENGTH: 12
<212> TYPE: PRT
<213> ORGANISM: homo sapiens

<400> SEQUENCE: 2

Gln Gly Met Ser Leu Cys Val Asp Pro Thr Gln Lys
1               5                   10
```